United States Patent [19]
Sohda et al.

[11] Patent Number: 5,650,410
[45] Date of Patent: Jul. 22, 1997

[54] PHARMACEUTICAL COMPOSITION CONTAINING QUINOLINE OR QUINAZOLINE DERIVATIVES AND DERIVATIVES THEREFOR

[75] Inventors: Takashi Sohda, Takatsuki; Haruhiko Makino, Kawabe-gun; Atsuo Baba, Ashiya, all of Japan

[73] Assignee: Takeda Chemical Industries, Ltd., Osaka, Japan

[21] Appl. No.: 416,708

[22] PCT Filed: Mar. 2, 1995

[86] PCT No.: PCT/JP95/00330

§ 371 Date: Apr. 17, 1995

§ 102(e) Date: Apr. 17, 1995

[87] PCT Pub. No.: WO95/24394

PCT Pub. Date: Sep. 14, 1995

[30] Foreign Application Priority Data

| Mar. 8, 1994 | [JP] | Japan | 6-036864 |
| Mar. 10, 1994 | [JP] | Japan | 6-039476 |
| Dec. 20, 1994 | [JP] | Japan | 6-316376 |

[51] Int. Cl.$^6$ ............ A61K 31/505; A61K 31/54; C07D 413/02; C07D 407/02
[52] U.S. Cl. ............ 514/233.8; 514/235.2; 514/259; 514/311; 514/314; 546/173; 544/115; 544/116; 544/283
[58] Field of Search ............ 544/283, 115, 544/116; 546/173; 514/259, 311, 233.8, 235.2, 314

[56] References Cited

U.S. PATENT DOCUMENTS

| 3,446,806 | 5/1969 | Archer et al. | 260/247.5 |
| 3,509,148 | 4/1970 | Bell | 260/251 |
| 4,089,953 | 5/1978 | Shenoy | 424/244 |
| 5,352,684 | 10/1994 | Zimmermann et al. | 514/299 |
| 5,436,247 | 7/1995 | Sohda et al. | 514/259 |

FOREIGN PATENT DOCUMENTS

| 0299727 | 1/1989 | European Pat. Off. . |
| 0567107 | 10/1993 | European Pat. Off. . |
| 0608870 | 8/1994 | European Pat. Off. . |
| 0634169 | 1/1995 | European Pat. Off. . |
| 2041361 | 9/1980 | United Kingdom . |

OTHER PUBLICATIONS

F. Gatta et al., "New Synthesis of 3–(Disubstituted–amino)–1,4–benzodiazepin–2–ones", Synthesis, 1979, No. 9, pp. 718–719.

M. Anzini et al., "Synthesis and 5HT–Receptors Affinity of some 4–phenylquinoline Derivatives", IL Farmaco, 1989, 44(6):555–563.

*Primary Examiner*—Matthew V. Grumbling
*Attorney, Agent, or Firm*—Foley & Lardner

[57] ABSTRACT

This invention provides an anti-inflammatory agent, particularly an agent for treating arthritis, containing a quinoline or quinazoline derivative or a salt thereof

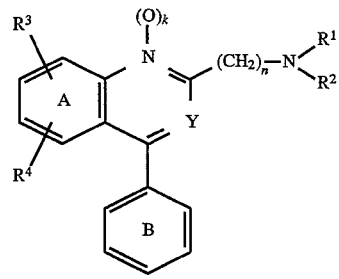

wherein
Y is a nitrogen atom or C—G in which G is an optionally esterified carboxyl group;

$R^1$ and $R^2$ are each independently a hydrogen atom, optionally substituted hydrocarbon group or optionally substituted heterocyclic group, or $R^1$ and $R^2$ are linked together to form a saturated ring;

each of the ring A and ring B may optionally be substituted;

n is an integer of 1 to 4; and k is 0 or 1.

This invention also provides a novel quinoline or quinazoline derivative having anti-inflammatory activity.

57 Claims, No Drawings

PHARMACEUTICAL COMPOSITION CONTAINING QUINOLINE OR QUINAZOLINE DERIVATIVES AND DERIVATIVES THEREFOR

This is a national stage application filed under 37 CFR 1.371 of international application PCT/JP9500330, filed Mar. 2, 1995.

TECHNICAL FIELD

The present invention relates to an anti-inflammatory agent. Specifically, it relates to an anti-inflammatory agent, particularly an agent for treating arthritis, containing a quinoline or quinazoline derivative or a salt thereof. The present invention also relates to a novel quinoline or quinazoline derivative having anti-inflammatory activity.

BACKGROUND ART

Arthritis is an inflammatory disease of arthroses. Main examples of arthritis are rheumatoid arthritis and its analogous diseases wherein inflammation is observed in arthroses.

In particular, rheumatoid arthritis, also referred to as chronic rheumatism, is polyarthritis chronica whose main lesion is inflammatory changes in synovial membranes of internal layers of articular capsules. Arthritis such as rheumatoid arthritis is progressive and causes articular disorders such as articular deformation, tetany, etc. When an effective treatment is not carried out and the disease worsens, serious physical disorders are often caused.

Hitherto, in treatment of such arthritis, chemotherapy has been carried out using steroids such as adrenal cortical hormones (e.g., cortisone, etc.), etc.; non-steroidal anti-inflammatory agents such as aspirin, piroxicam, indomethacin, etc.; gold preparations such as gold thiomalate, etc.; antirheumatic agents such as chloroquine preparations, D-penicillamine, etc.; antipodagrics such as colchicine, etc.; immunosuppressive agents such as cyclophosphamide, azathioprine, methotrexate, levamisole, etc.

However, drugs using the chemotherapy have problems such as serious side effects, side effects making their long-term use difficult, insufficient efficacy, inefficacy against arthritis which has already produced the symptoms.

Therefore, in clinical treatment of arthritis, drugs having low toxicity and excellent effects in the prophylaxis and treatment of arthritis have been required.

Various quinoline or quinazoline derivatives have been synthesized. Known compounds having an aminomethyl group at the 2 position of the 4-phenylquinoline or 4-phenylquinazoline skeleton are 2-dimethylaminomethyl compounds, 2-morpholinomethyl compounds, etc., described in Synthesis, Vol. 9, p. 718 (1979), and 2-alkylaminomethyl quinoline derivatives, etc., described in Farmaco, Vol. 44, p. 555 (1989). However, none of these literature discloses anti-inflammatory activity of 4-phenylquinoline or 4-phenylquinazoline derivatives.

The main object of the present invention is to provide an anti-inflammatory pharmaceutical composition.

Another object of the present invention is to provide a novel quinoline or quinazoline derivative having anti-inflammatory activity.

These objects as well as other objects and advantages of the present invention will become apparent to those skilled in the art from the following description.

DISCLOSURE OF INVENTION

The present inventors have found that compounds containing at the 2-position of the 4-phenylquinoline or 4-phenylquinazoline skeleton an alkylene group substituted with an optionally substituted amino group have anti-inflammatory activity, particularly antiarthritic activity, and are useful as an agent for inhibiting arthral destruction. Thus, the present invention has been completed.

The present invention provides an anti-inflammatory pharmaceutical composition comprising a compound of the formula (I):

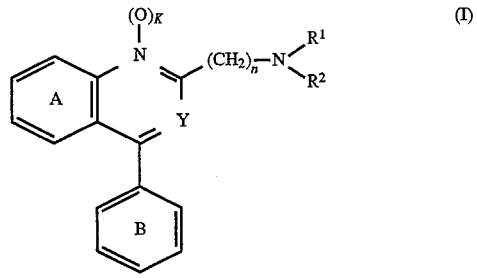

wherein,

Y is a nitrogen atom or C—G in which G is an optionally esterified carboxyl group;

$R^1$ and $R^2$ are each independently a hydrogen atom, optionally substituted hydrocarbon group or optionally substituted heterocyclic group or $R^1$ and $R^2$ are linked together to form a saturated ring;

each of the ring A and ring B may optionally be substituted;

n is an integer of 1 to 4; and k is 0 or 1;

or a pharmaceutically acceptable salt thereof and a pharmaceutically acceptable carrier.

The present invention also provides a compound of the formula (I'):

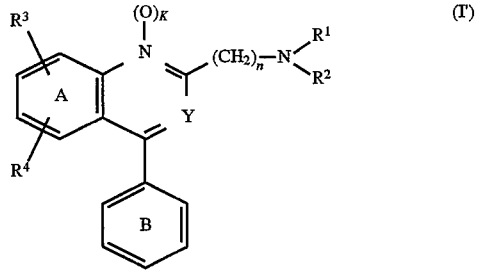

wherein

Y is a nitrogen atom or C—G in which G is an optionally esterified carboxyl group;

$R^1$ and $R^2$ are each independently a hydrogen atom, optionally substituted hydrocarbon group or optionally substituted heterocyclic group, or $R^1$ and $R^2$ are linked together to form a saturated ring;

$R^3$ and $R^4$ are each independently an alkoxy group;

the ring B may optionally be substituted;

n is an integer of 1 to 4; and k is 0 or 1;

or a salt thereof

The compound of the formula (I) includes several novel compounds, for example, novel compounds of the formula (I').

The symbols in the above formulas are defined and exemplified as follows.

The hydrocarbon group of the optionally substituted hydrocarbon group represented by $R^1$ or $R^2$ in the above formulas (I) and (I') includes aliphatic hydrocarbon groups, alicyclic hydrocarbon groups, alicyclic-aliphatic hydrocarbon groups, (aromatic carbocycle)-aliphatic hydrocarbon groups, aromatic hydrocarbon groups and the like.

Examples of such aliphatic hydrocarbon groups include saturated aliphatic hydrocarbon groups having 1 to 8 carbon atoms such as methyl, ethyl, propyl, isopropyl, butyl, isobutyl, sec-butyl, tert-butyl, pentyl, isopentyl, neopentyl, tert-pentyl, hexyl, isohexyl, heptyl, octyl and the like; unsaturated aliphatic hydrocarbon groups having 2 to 8 carbon atoms such as ethenyl, 1-propenyl, 2-propenyl, 1-butenyl, 2-butenyl, 3-butenyl, 2-methyl-1-propenyl, 1-pentenyl, 2-pentenyl, 3-pentenyl, 4-pentenyl, 3-methyl-2-butenyl, 1-hexenyl, 3-hexenyl, 2,4-hexadienyl, 5-hexenyl, 1-heptenyl, 1-octenyl, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 3-hexynyl, 2,4-hexadiynyl, 5-hexynyl, 1-heptynyl, 1-octynyl and the like.

Examples of such alicyclic hydrocarbon groups include saturated alicyclic hydrocarbon groups having 3 to 7 carbon atoms such as cyclopropyl, cyclobutyl, cyclopentyl, cyclohexyl, cycloheptyl and the like; and unsaturated alicyclic hydrocarbon groups having 5 to 7 carbon atoms such as 1-cyclopentenyl, 2-cyclopentenyl, 3-cyclopentenyl, 1-cyclohexenyl, 2-cyclohexenyl, 3-cyclohexenyl, 1-cycloheptenyl, 2-cycloheptenyl, 3-cycloheptenyl, 2,4-cycloheptadienyl and the like.

Examples of such alicyclic-aliphatic hydrocarbon groups include those having 4 to 9 carbon atoms each of which is composed of the above alicyclic hydrocarbon group and aliphatic hydrocarbon group, for example, cyclopropylmethyl, cyclopropylethyl, cyclobutylmethyl, cyclopentylmethyl, 2-cyclopentenylmethyl, 3-cyclopentenylmethyl, cyclohexylmethyl, 2-cyclohexenylmethyl, 3-cyclohexenylmethyl, cyclohexylethyl, cyclohexylpropyl, cycloheptylmethyl, cycloheptylethyl and the like.

Examples of such (aromatic carbocycle)-aliphatic hydrocarbon groups include phenylalkyl having 7 to 9 carbon atoms such as benzyl, phenethyl, 1-phenylethyl, 3-phenylpropyl, 2-phenylpropyl, 1-phenylpropyl and the like; naphthylalkyl having 11 to 13 carbon atoms such as α-naphthylmethyl, α-naphtylethyl, β-naphthylmethyl, β-naphthylethyl and the like.

Examples of such aromatic hydrocarbon groups include phenyl, naphthyl (e.g., α-naphthyl, β-naphthyl) and the like.

The heterocyclic group of the optionally substituted heterocyclic group represented by $R^1$ or $R^2$ in the above formulas (I) and (I') includes 5- to 7-membered heterocyclic groups containing one sulfur atom, nitrogen atom or oxygen atom; 5- to 6-membered heterocyclic groups containing 2 to 4 nitrogen atoms; 5- to 6-membered heterocyclic groups containing 1 to 2 nitrogen atoms, and one sulfur atom or oxygen atom. Each of these heterocyclic groups may form a condensed ring with a 6-membered ring containing up to 2 nitrogen atoms, benzene ring or 5-membered ring containing one sulfur atom.

Specific examples of the heterocyclic group include 2-pyridyl, 3-pyridyl, 4-pyridyl, 2-pyrimidinyl, 4-pyrimidinyl, 5-pyrimidinyl, 6-pyrimidinyl, 3-pyridazinyl, 4-pyridazinyl, 2-pyrazinyl, 2-pyrrolyl, 3-pyrrolyl, 2-imidazolyl, 4-imidazolyl, 5-imidazolyl, 3-pyrazolyl, 4-pyrazolyl, isothiazolyl, isoxazolyl, 2-thiazolyl, 4-thiazolyl, 5-thiazolyl, 2-oxazolyl, 4-oxazolyl, 5-oxazolyl, 1,2,4-triazol-3-yl, 1,2,3-triazol-4-yl, tetrazol-5-yl, benzimidazol-2-yl, indol-3-yl, 1H-indazol-3-yl, 1H-pyrrolo[2,3-b]pyrazin-2-yl, 1H-pyrrolo[2,3-b]pyridin-6-yl,1H-imidazo[4,5-b]pyridin-2-yl, 1H-imidazo[4,5-c]pyridin-2-yl, 1H-imidazo[4,5-b]pyrazin-2-yl and the like.

Each of the hydrocarbon groups and heterocyclic groups represented by $R^1$ or $R^2$ in the above formulas (I) and (I') may be unsubstituted or substituted with 1 to 3 substituents at any possible position in the ring.

The substituents of the hydrocarbon group or heterocyclic group represented by $R^1$ or $R^2$ include, for example, aliphatic chain hydrocarbon groups, alicyclic hydrocarbon groups, aryl groups, aromatic heterocyclic groups, non-aromatic heterocyclic groups, halogen atoms, nitro group, optionally substituted amino group, optionally substituted acyl groups, optionally substituted hydroxyl group, optionally substituted thiol group, optionally esterified carboxyl group and the like.

The aliphatic chain hydrocarbon group as the substituent of the hydrocarbon group or heterocyclic group represented by $R^1$ or $R^2$ include, for example, straight chain or branched aliphatic hydrocarbon groups such as alkyl groups, preferably alkyl groups having 1 to 10 carbon atoms; alkenyl groups, preferably alkenyl groups having 2 to 10 carbon atoms; alkynyl groups and the like.

Preferred examples of the alkyl group include methyl, ethyl, propyl, isopropyl, butyl, isobutyl, sec-butyl, tert-butyl, pentyl, isopentyl, neopentyl, tert-pentyl, 1-ethylpropyl, hexyl, isohexyl, 1,1-dimethylbutyl, 2,2-dimethylbutyl, 3,3-dimethylbutyl, 2-ethylbutyl, hexyl, pentyl, octyl, nonyl, decyl and the like.

Preferred examples of the alkenyl group include vinyl, allyl, isopropenyl, 1-propenyl, 2-methyl-1-propenyl, 1-butenyl, 2-butenyl, 3-butenyl, 2-ethyl-1-butenyl, 3-methyl- 2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl and the like.

Preferred examples of the alkynyl groups include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and the like.

The alicyclic hydrocarbon group as the substituent of the hydrocarbon group or heterocyclic group represented by $R^1$ or $R^2$ include, for example, saturated or unsaturated alicyclic hydrocarbon groups such as cycloalkyl groups, cycloalkenyl groups, cycloalkadienyl groups and the like.

Preferred examples of the cycloalkyl groups include those having 3 to 10 carbon atoms such as cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, bicyclo[3.2.2]nonyl, bicyclo[3.3.1]nonyl, bicyclo[4.2.1]nonyl, bicyclo[4.3.1]decyl and the like.

Preferred examples of the cycloalkenyl groups include those having 3 to 7 carbon atoms such as 2-cyclopenten-1-yl, 3-cyclopenten-1-yl, 2-cyclohexen-1-yl, 3-cyclohexen-1-yl and the like.

Preferred examples of the cycloalkadienyl groups include those having 5 to 8 carbon atoms such as 2,4-cyclopentadien-1-yl, 2,4-cyclohexadien-1-yl, 2,5-cyclohexadien-1-yl and the like.

The aryl group as the substituent of the hydrocarbon group or heterocyclic group represented by $R^1$ or $R^2$ means a monocyclic or condensed polycyclic aromatic hydrocarbon group. Preferred examples thereof include phenyl, naphthyl, anthryl, phenanthryl, acenaphthylenyl and the like. More preferred examples thereof are phenyl, 1-naphthyl, 2-naphthyl and the like.

Preferred examples of the aromatic heterocyclic group as the substituent of the hydrocarbon group or heterocyclic group represented by $R^1$ or $R^2$ include aromatic monocyclic heterocyclic groups such as furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl and the like: aromatic condensed heterocyclic groups such as benzofuranyl, isobenzofuranyl, benzo[b]thienyl, indolyl, isoindolyl, 1H-indazolyl, benzimidazolyl, benzoxazolyl, 1,2-benzisoxazolyl, benzothiazolyl, 1,2-benzisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl and the like.

Preferred examples of the non-aromatic heterocyclic group as the substituent of the hydrocarbon group or heterocyclic group represented by $R^1$ or $R^2$ include oxiranyl, azetidinyl, oxetanyl, thietanyl, pyrrolidinyl, tetrahydrofuryl, thiolanyl, piperidyl, tetrahydropyranyl, morpholinyl, thiomorpholinyl, piperazinyl and the like.

The halogen atom as the substituent of the hydrocarbon group or heterocyclic group represented by $R^1$ or $R^2$ includes, for example, fluorine, chlorine, bromine and iodine. In particular, fluorine and chlorine are preferred.

The optionally substituted amino group as the substituent of the hydrocarbon group or heterocyclic group represented by $R^1$ or $R^2$ includes, for example, an amino group and an amino group substituted with one or two substituents such as alkyl groups having 1 to 10 carbon atoms, alkenyl groups having 2 to 10 carbon atoms, aromatic groups, heterocyclic groups or acyl groups having 1 to 10 carbon atoms (e.g., methylamino, dimethylamino, ethylamino, diethylamino, dibutylamino, diallylamino, cyclohexylamino, phenylamino, N-methyl-N-phenylamino, acetylamino, propionylamino, benzoylamino, nicotinoylamino, etc.).

The acyl group as the substituent of hydrocarbon group or heterocyclic group represented by $R'$ or $R^2$ includes, for example, formyl, and ($C_{1-10}$ alkyl)-carbonyl, ($C_{2-10}$ alkenyl) carbonyl and aromatic carbonyl (e.g., acetyl, propionyl, butyryl, isobutyryl, valeryl, isovaleryl, pivaloyl, hexanoyl, heptanoyl, octanoyl, cyclobutanecarbonyl, cyclopentanecarbonyl, cyclohexanecarbonyl, cycloheptanecarbonyl, crotonyl, 2-cyclohexenecarbonyl, benzoyl, nicotinoyl, etc.).

The optionally substituted hydroxyl group as the substituent of the hydrocarbon group or heterocyclic group represented by $R^1$ or $R^2$ includes, for example, a hydroxyl group and a hydroxyl group having an appropriate substituent such as a protecting group for a hydroxyl group. Examples of the hydroxyl group having such a substituent include alkoxy, alkenyloxy, aralkyloxy, acyloxy, aryloxy and the like.

Preferred examples of the alkoxy include that having 1 to 10 carbon atoms such as methoxy, ethoxy, propoxy, isopropoxy, butoxy, isobutoxy, sec-butoxy, tert-butoxy, pentyloxy, isopentyloxy, neopentyloxy, hexyloxy, heptyloxy, nonyloxy, cyclobutyloxy, cyclopentyloxy, cyclohexyloxy and the like.

Examples of the alkenyloxy include that having 2 to 10 carbon atoms such as allyloxy, crotyloxy, 2-pentenyloxy, 3-hexenyloxy, 2-cyclopentenylmethoxy, 2-cyclohexenylmethoxy and the like.

Examples of the aralkyloxy include phenyl-$C_{1-4}$ alkyloxy (e.g., benzyloxy, phenethyloxy, etc.).

Preferred examples of the acyloxy include alkanoyloxy having 2 to 4 carbon atoms such as acetyloxy, propionyloxy, butyryloxy, isobutyryloxy and the like.

Examples of the aryloxy include phenoxy, 4-chlorophenoxy and the like.

The optionally substituted thiol group as the substituent of the hydrocarbon group or heterocyclic group represented by $R^1$ or $R^2$ includes, for example, a thiol group and a thiol group having an appropriate substiuent such as a protecting group for a thiol group. Examples of the thiol group having such a substituent include alkylthio, aralkylthio, acylthio and the like.

Preferred examples of the alkylthio include alkylthio having 1 to 10 carbon atoms such as methylthio, ethylthio, propylthio, isopropylthio, butylthio, isobutyltho, sec-butylthio, tert-butylthio, pentylthio, isopentylthio, neopentylthio, hexylthio, heptylthio, nonylthio, cyclobutylthio, cyclopentylthio, cyclohexylthio and the like.

Examples of the aralkylthio include phenyl-$C_{1-4}$ alkylthio (e.g., benzylthio, phenetylthio, etc.).

Preferred examples of the acylthio include alkanoylthio having 2 to 4 carbon atoms such as acetylthio, propionylthio, butyrylthio, isobutyrylthio and the like.

The optionally esterified carboxyl group as the substituent of the hydrocarbon group or heterocyclic group represented by $R'$ or $R^2$ include, for example, a carboxyl group, alkyloxycarbonyl, and aralkyloxycarbonyl.

The alkyl group of the alkyloxycarbonyl includes alkyl groups having 1 to 6 carbon atoms such as methyl, ethyl, propyl, isopropyl, butyl, isobutyl, sec-butyl, tert-butyl, etc.

The aralkyl group of the aralkyloxycarbonyl means an aryl-alkyl group. The aryl group of the aryl-alkyl group includes phenyl and naphthyl, and the aryl group may have the above substituent(s) of the above hydrocarbon group represented by $R^1$ or $R^2$. Preferred examples of the alkyl group of the aryl-alkyl group include lower alkyl groups having 1 to 6 carbon atoms such as methyl, ethyl, propyl, butyl, etc. Preferred examples of the aralkyl group include benzyl, phenethyl, 3-phenylpropyl, (1-naphthyl)methyl, (2-naphthyl)methyl, etc. In particular, benzyl and phenethyl are preferred.

The substituent of the hydrocarbon group and heterocyclic group represented by $R^1$ or $R^2$ in the above formula (I) and (I') may have at least one, preferably 1 to 3, appropriate substituents. The substituents include:

lower ($C_{1-8}$) alkyl groups such as methyl, ethyl, propyl, isopropyl, butyl, isobutyl, sec-butyl, tert-butyl, pentyl, isopentyl, neopentyl, tert-pentyl, hexyl, isohexyl, heptyl, octyl, etc.;

lower ($C_{2-10}$) alkenyl groups such as ethenyl, 1-propenyl, 2-propenyl, 1-butenyl, 2-butenyl, 3-butenyl, 2-methyl-1-propenyl, 1-pentenyl, 2-pentenyl, 3-pentenyl, 4-pentenyl, 3-methyl-2-butenyl, 1-hexenyl, 3-hexenyl, 2,4-hexadienyl, 5-hexenyl, 1-heptenyl, 1-octenylvinyl, etc.;

lower ($C_{2-8}$) alkynyl groups such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 3-hexynyl, 2,4-hexadiynyl, 5-hexynyl, 1-heptynyl, 1-octynyl, etc.;

$C_{3-8}$ cycloalkyl groups such as cyclopropyl, cyclobutyl, cyclopentyl, cyclohexyl, cycloheptyl, etc.;

$C_{6-15}$ aryl groups such as phenyl, naphthyl (e.g., 1-naphthyl, 2-naphthyl, etc), anthryl, phenanthryl, acenaphthylenylphenyl, etc.;

aromatic heterocyclic groups such as aromatic monocyclic heterocyclic groups (e.g., furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl, etc.), aromatic condensed heterocyclic groups (e.g., benzofuranyl, isobenzofuranyl, benzo[b]thienyl, indolyl, isoindolyl, 1H-indazolyl, benzimidazolyl, benzoxazolyl, 1,2-benzisoxazolyl, benzothiazolyl, 1,2-benzisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl, etc.), etc.;

non-aromatic heterocyclic groups such as oxiranyl, azetidinyl, oxetanyl, thietanyl, pyrrolidinyl, tetrahydrofuryl, thiolanyl, piperidyl, tetrahydropyranyl, morpholinyl, thiomorpholinyl, piperazinyl, etc.;

aralkyl groups, preferably $C_{6-14}$-aryl-$C_{1-4}$ alkyl groups, such as benzyl, phenetyl, 3-phenylpropyl, (1-naphthyl)methyl, (2-naphthyl)methyl, etc.;

an amino group;

N-monosubstituted amino groups such as methylamino, ethylamino, butylamino, allylamino, cyclohexylamino, phenylamino, acetylamino, propionylamino, benzoylamino, nicotinoylamino, etc.;

N,N-disubstituted amino groups such as dimethylamino, diethylamino, dibutylamino, diallylamino, N-methyl-N-phenylamino, etc.;

an amidino group;

$C_{1-10}$ acyl groups such as formyl, acetyl, propionyl, butyryl, isobutyryl, valeryl, isovaleryl, pivaloyl, hexanoyl, heptanoyl, octanoyl, cyclobutanecarbonyl, cyclopentanecarbonyl, cyclohexanecarbonyl, cycloheptanecarbonyl, crotonyl, 2-cyclohexenecarbonyl, benzoyl, nicotinoyl, etc.;

a carbamoyl group;

N-monosubstituted carbamoyl groups such as methylcarbamoyl, ethylcarbamoyl, phenylcarbamoyl, etc.;

N,N-disubstituted carbamoyl groups such as N,N-dimetylcarbamoyl, N,N-diethylcarbamoyl, piperidinocarbonyl, morpholinocarbonyl, etc.;

a sulfamoyl group;

N-monosubstituted sulfamoyl groups such as methylsulfamoyl, ethylsulfamoyl, phenylsulfamoyl, p-toluenesulfamoyl, etc.; N,N-disubstituted sulfamoyl groups such as N,N-dimethylsulfamoyl, N-methyl-N-phenylsulfamoyl, piperidinosulfonyl, morpholinosulfonyl, etc.;

a carboxyl group;

lower ($C_{1-5}$) alkoxy-carbonyl groups such as methoxycarbonyl, ethoxycarbonyl, propoxycarbonyl, isopropoxycarbonyl, sec-butyloxycarbonyl, isobutoxycarbonyl, tert-butyloxycarbonyl, etc.;

a hydroxy group;

lower ($C_{1-8}$) alkoxy groups such as methoxy, ethoxy, propoxy, isopropoxy, butoxy, isobutoxy, sec-butoxy, tert-butoxy, pentyloxy, isopentyloxy, neopentyloxy, hexyloxy, heptyloxy, nonyloxy, cyclobutoxy, cyclopentoxy, cyclohexyloxy, etc.;

lower ($C_{3-10}$) alkenyloxy groups such as allyloxy, crotyloxy, 2-pentenyloxy, 3-hexenyloxy, 2-cyclopentenylmethoxy, 2-cyclohexenylmethoxy, etc.;

$C_{3-7}$ cycloalkyloxy groups such as cyclopropyloxy, cyclobutyloxy, cyclopentyloxy, cyclohexyloxy, cycloheptyloxy, etc.;

aralkyloxy, preferably $C_{6-14}$ aryl-$C_{1-4}$ alkyloxy, such as benzyloxy, phenethyloxy 3-phenylpropyloxy, (1-naphthyl)methyloxy, (2-naphthyl)methyloxy, etc.;

$C_{6-15}$ aryloxy such as phenoxy, naphtyloxy (e.g., 1-naphtyloxy, 2-naphtyloxy, etc.), anthryloxy, phenanthryloxy, acenaphtylenylphenyloxy, etc.;

a mercapto group;

lower ($C_{1-8}$) alkylthio groups such as methylthio, ethylthio, propylthio, isopropylthio, butylthio, isobutylthio, sec-butylthio, tert-butylthio, pentylthio, isopentylthio, neopentylthio, hexylthio, heptylthio, nonylthio, cyclobutylthio, cyclopentylthio, cyclohexylthio, etc.;

$C_{6-14}$ aryl-$C_{1-4}$ alkylthio groups such as benzylthio, phenethylthio, etc.;

$C_{6-14}$ arylthio groups such as phenylthio, naphtylthio (1-naphtylthio, 2-naphtylthio, etc.), anthrylthio, phenanthrylthio, acenaphthylenylphenylthio, naphthylthio, etc.;

a sulfo group;

a cyano group;

an azido group;

a nitro group;

a nitroso group;

a halogen atom such as fluorine, chlorine, bromine and iodine; etc.

When $R^1$ and $R^2$ is linked together to form a saturated ring, the group of —N($R^1$)($R^2$) is, for example, 1-pyrrolidinyl, 1-imidazolidinyl, 1-pyrazolidinyl, 1-piperidinyl, 1-piperazinyl, 4-morpholinyl, 4-thiomorpholinyl, homopiperazin-1-yl, etc. The saturated ring may contain an oxo group or thioxo group.

When the compound of the formula (I) is a quinoline derivative wherein Y is C—G, the esterified carboxyl group represented by G includes, for example, alkyloxycarbonyl groups, and aralkyloxycarbonyl groups.

The alkyl group of the alkyloxycarbonyl group includes, for example, alkyl groups having 1 to 6 carbon atoms such as methyl, ethyl, propyl, isopropyl, butyl, isobutyl, sec-butyl, tert-butyl, etc. In particular, ethyl is preferred.

The aralkyl group of the aralkyloxycarbonyl group means an alkyl group having an aryl group as a substituent (i.e., arylalkyl group). The aryl of group includes $C_{6-14}$ aryl groups such as phenyl, naphthyl, etc. The aryl group may have the above substituent of the aryl group of the hydrocarbon group represented by $R^1$ or $R^2$. The alkyl group is preferably a lower alkyl group having 1 to 6 carbon atoms. Preferred examples of the aralkyl group include benzyl, phenethyl, 3-phenylpropyl, (1-naphthyl)methyl, (2-naphthyl)methyl, etc. In particular, benzyl and phenethyl are preferred.

Each of the ring A and ring B in the formula (I) may be substituted with at least one substituent. Examples of the substituent include halogen atoms, a nitro group, optionally substituted alkyl groups, an optionally substituted hydroxyl group, an optionally substituted thiol group, an optionally substituted amino group, optionally substituted acyl groups, an optionally esterified carboxyl group and optionally substituted aromatic cyclic groups.

The halogen atom as the substituent of the ring A and ring B includes, for example, fluorine, chlorine, bromine and iodine. In particular, fluorine and chlorine are preferred.

The optionally substituted alkyl group as the substituent of the ring A and ring B may be straight-chain, branched or cyclic alkyl groups. Specific examples thereof include methyl, ethyl, propyl, isopropyl, butyl, isobutyl, sec-butyl, tert-butyl, pentyl, isopentyl, neopentyl, hexyl, heptyl, octyl, nonyl, decyl, cycloproyl, cyclobutyl, cyclopentyl, cyclohexyl, cycloheptyl, etc.

The optionally substituted hydroxyl group as the substituent of the ring A and ring B includes, for example, a hydroxyl group and a hydroxyl group having an appropriate substituent such as that used as a protecting group for a hydroxyl group (e.g., alkoxy, alkenyloxy, aralkyloxy, acyloxy, aryloxy, etc.).

Preferred examples of the alkoxy include that having 1 to 10 carbon atoms such as methoxy, ethoxy, propoxy, isopropoxy, butoxy, isobutoxy, sec-butoxy, tert-butoxy, pentyloxy, isopentyloxy, neopentyloxy, hexyloxy, heptyloxy, nonyloxy, cyclobutyloxy, cyclopentyloxy, cyclohexyloxy, etc.

Examples of the alkenyloxy include that having 2 to 10 carbon atoms such as allyloxy, crotyloxy, 2-pentenyloxy, 3-hexenyloxy, 2-cyclopentenylmethoxy, 2-cyclohexenylmethoxy, etc.

Examples of the aralkyloxy include phenyl-$C_{1-4}$ alkyloxy (e.g., benzyloxy, phenethyloxy, etc.).

Preferred examples of the acyloxy include alkanoyloxy having 2 to 4 carbon atoms such as acetyloxy, propionyloxy, butyryloxy, isobutyryloxy, etc.

Examples of the aryloxy include $C_{6-14}$ aryloxy such as phenoxy, and 4-chlorophenoxy.

The optionally substituted thiol as the substituent of the ring A and ring B includes, for example, a thiol group and a thiol group having an appropriate substituent such as that used as a protecting group for a thiol group (e.g., alkylthio, aralkylthio, acylthio, etc.).

Preferred examples of the alkylthio include that having 1 to 10 carbon atoms such as methylthio, ethylthio, propylthio, isopropylthio, butylthio, isobutylthio, sec-butylthio, tert-butylthio, pentylthio, isopentylthio, neopentylthio, hexylthio, heptylthio, nonylthio, cyclobutylthio, cyclopentylthio, cyclohexylthio, etc.

Examples of the aralkylthio include phenyl-$C_{1-4}$ alkylthio (e.g., benzylthio, phenethylthio, etc.).

Preferred examples of the acylthio include alkanoylthio having 2 to 4 carbon atoms such as acetylthio, propionylthio, butyrylthio, and iso-butyrylthio.

The optionally substituted amino group as the substituent of the ring A and ring B includes, for example, an amino group and an amino group substituted with one or two substituents selected from alkyl groups having 1 to 10 carbon atoms, alkenyl groups having 2 to 10 carbon atoms, aromatic groups, and acyl groups. Specific examples of the substituted amino group include methylamino, dimethylamino, ethylamino, diethylamino, dibutylamino, diallylamino, cyclohexylamino, phenylamino, N-methyl-N-phenylamino, acetylamino, propionylamino, benzoylamino, etc.

The optionally substituted acyl group as the substituent of the ring A and ring B include, for example, formyl, and ($C_{1-10}$ alkyl)-carbonyl, ($C_{2-10}$ alkenyl)-carbonyl and (aromatic group)-carbonyl such as acetyl, propionyl, butyryl, isobutyryl, valeryl, isovaleryl, pivaloyl, hexanoyl, heptanoyl, octanoyl, cyclobutanecarbonyl, cyclopentanecarbonyl, cyclohexanecarbonyl, cycloheptanecarbonyl, crotonyl, 2-cyclohexenecarbonyl benzoyl, nicotinoyl, etc.

The optionally substituted aromatic cyclic group as the substituent of the ring A and ring B includes, for example, $C_{6-14}$ aromatic hydrocarbon groups (e.g., phenyl, naphthyl, anthryl, etc.) and aromatic heterocyclic groups (e.g., pyridyl, furyl, thienyl, imidazolyl, thiazolyl, etc.). The substituent includes the above substituents of the hydrocarbon group represented by $R^1$ or $R^2$.

The substituent of the ring A and ring B may be at any possible position in each of the rings. Preferably, the ring A is substituted at the 6 and/or 7 positions of the quinoline or quinazoline ring. Preferably, the ring B is substituted at the 3 and/or 4 positions of the ring B. The each of the rings may be substituted with the same or different 1 to 4 substituents. When the substituents of the ring A or ring B are adjacent to each other, the adjacent substituents are linked together to form a group of the formula: —$(CH_2)_m$— or —O—$(CH_2)_l$—O— (wherein m is an integer of 3 to 5 and l is an integer of 1 to 3) which may form a 5- to 7-membered ring with carbon atoms of the benzene ring.

Preferably, the ring A is substituted with lower ($C_{1-3}$) alkylenedioxy groups, in particular methylenedioxy, at the 6- and 7-positions of the quinoline or quinazoline ring; the same or different alkoxy groups, in particular methoxy; or the same or different two alkoxy groups, in particular two methoxy groups, at the 6- and 7-positions of the quinoline or quinazoline ring.

Preferably, the ring B is substituted with lower ($C_{1-3}$) alkylenedioxy groups, in particular methylenedioxy; at least one alkoxy group, in particular methoxy; the same or different two alkoxy groups, in particular two methoxy groups; methoxy groups at the 3- or 4-position; or two methoxy groups at the 3- and 4-positions.

The ring A in the formula (I') is substituted with the same or different alkoxy groups represented by $R^3$ and $R^4$. Examples of alkoxy groups represented by $R^3$ and $R^4$ include the alkoxy groups described above for the alkoxy group as the substituent of the ring A and ring B in the formula (I). When the ring B in the formula (I') is substituted, the substituents include the substituents of the ring A and ring B in the formula (I).

n in the formula (I) is preferably 1 or 2, more preferably 1.

k in the formula (I) is preferably 0.

Preferred examples of the compound of the formula (I) include:

ethyl 4-(3,4-dimethoxyphenyl)-2-(N-sec-butyl-N-propylaminomethyl)-6,7-dimethoxyquinoline-3-carboxylate (compound of Example 39);

ethyl 4-(3,4-dimethoxyphenyl)-2-(N-tert-butyl-N-ethylaminomethyl)-6,7-dimethoxyquinoline-3-carboxylate (compound of Example 40);

ethyl 2-(N,N-diethylaminomethyl)-4-(3,4-dimethoxyphenyl)-6,7-dimethoxyquinoline-3-carboxylate (compound of Example 5); and 4-(3,4-dimethoxyphenyl)-2-(N-ethylaminomethyl)-6,7-dimethoxyquinazoline (compound of Example 54).

The salts of the compounds of the formulas (I) and (I') used in the present invention is preferably a pharmaceutically acceptable salt. Examples thereof include salts with inorganic bases, organic bases, inorganic acids, organic acids, basic or acidic amino acids and the like.

Preferred examples of the salts with inorganic bases include alkaline metal salts such as a sodium salt, potassium salt, etc.; alkaline earth metal salts such as a calcium salt, magnesium salt, etc.; an aluminium salt, etc.; an ammonium salt, etc.

Preferred examples of the salts with organic bases include salts with trimethylamine, triethylamine, pyridine, picoline, ethanolamine, diethanolamine, triethanolamine, dicyclohexylamine, N,N'-dibenzylethylenediamine, etc.

Preferred examples of the salts with inorganic acids include salts with hydrochloric acid, hydrobromic acid, nitric acid, sulfuric acid, phosphoric, etc.

Preferred examples of the salts with organic acids include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, etc.

Preferred examples of the salts with basic amino acids include salts with arginine, lysine, ornithine, etc.

Preferred examples of the salts with acidic amino acids include aspartic acid, glutamic acid, etc.

The compound of the formula (I) used in the present invention can be formulated with a pharmaceutically acceptable carrier and administered orally or parenterally as solid preparations such as tablets, capsules, granules, powders, etc; or liquid preparations such as syrups, injections, etc.

As the pharmaceutically acceptable carrier, various organic or inorganic carrier materials conventionally used for pharmaceutical preparations can be used, and formulated as excipients, lubricants, binders, disintegrators, etc., for solid preparations; solvents, solution adjuvants, suspending agents, tonicity agents, buffering agents, soothing agents, etc., for liquid preparations. If necessary, pharmaceutical additives such as antiseptics, antioxidants, colorants, sweetening agents, etc., can be used.

Preferred examples of the excipient include lactose, sucrose, D-mannitol, starch, crystalline cellulose, light anhydrous silicic acid, etc.

Preferred examples of the lubricant include magnesium stearate, calcium stearate, talc, colloidal silica, etc.

Preferred examples of the binder include crystalline cellulose, sucrose, D-mannitol, dextrin, hydroxypropylcellulose, hydroxypropylmethylcellulose, polyvinylpyrrolidone, etc.

Preferred examples of the disintegrator include starch, carboxymethylcellulose, carboxymethyl cellulose calcium, croscarmellose sodium, carboxymethyl starch sodium, etc.

Preferred examples of the solvent include water for injection, alcohols, propylene glycol, macrogol, sesame oil, corn oil, etc.

Preferred examples of the solution adjuvant include polyethylene glycol, propylene glycol, D-mannitol, benzyl benzoate, ethanol, trisaminomethane, cholesterol, triethanolamine, sodium carbonate, sodium citrate, etc.

Preferred examples of the suspending agent include surfactants such as stearyl triethanolamine, sodium lauryl sulfate, laurylaminopropionic acid, lecithin, benzalkonium chloride, benzethonium chloride, glyceryl monostearate, etc.; hydrophilic polymers such as polyvinyl alcohol, polyvinyl pyrrolidone, carboxymethylcellulose sodium, methylcellulose, hydroxymethylcellulose, hydroxyethylcellulose, hydroxypropylcellulose, etc.

Preferred examples of the tonicity agent include sodium chloride, glycerin, D-mannitol, etc.

Preferred examples of the buffering agent include buffers such as phosphates, acetates, carbonates, citrates, etc.

Preferred examples of the soothing agent include benzyl alcohol, etc.

Preferred examples of the antiseptics include parahydroxybenzoic acid esters, chlorobutanol, benzyl alcohol, phenethyl alcohol, dehydroacetic acid, sorbic acid, etc.

Preferred examples of the antioxidant include sulfites, ascorbic acid, etc.

The compound (I) (i.e., the compound of the formula (I); the compounds of the other formulas are hereinafter sometimes abbreviated likewise) can be prepared, for example, as follows.

Method A

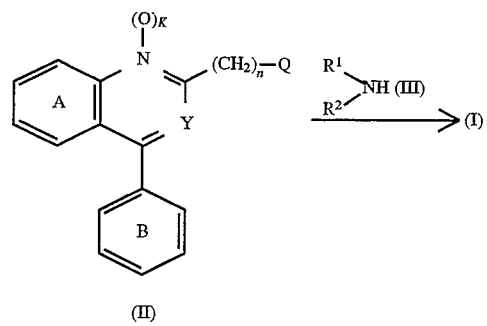

wherein Q is a leaving group, and the other symbols are as defined above.

The leaving group represented by Q in the formula (II) includes, for example, halogen (preferably chlorine, bromine, iodine), a hydroxy group activated by esterification such as an organic sulfonic acid residue (e.g., p-toluenesulfonyloxy, methanesulfonyloxy, etc.) and an organic phosphoric acid residue (e.g., diphenylphosphoryloxy, dibenzylphosphoryloxy, dimethylphosphoryloxy, etc.).

In this method, the compound (II) is reacted with the compound (III) in the presence of a base to prepare the compound (I). The reaction of the compound (II) with the compound (III) can be carried out in an appropriate solvent. Examples of the solvent include aromatic hydrocarbons (e.g., benzene, toluene, xylene, etc.), ethers (e.g., dioxane, tetrahydrofuran, dimethoxyethane, etc.), alcohols (e.g., methanol, ethanol, propanol, etc.), ethyl acetate, acetonitrile, pyridine, N,N-dimethylformamide, dimethyl sulfoxide, chloroform, dichloromethane, 1,2-dichloroethane, 1,1,2,2-tetrachloroethane, acetone and 2-butanone, and mixed solvents thereof.

The reaction of the compound (II) with the compound (III) can be carried out in the presence of an appropriate base such as alkaline metal salts (e.g., sodium hydroxide, potassium hydroxide, potassium carbonate, sodium carbonate, sodium bicarbonate, etc.), amines (e.g., pyridine, triethylamine, N,N-dimethylaniline, etc.), sodium hydride, potassium hydride, etc. The amount of the base to be used is preferably 1 to 5 mol per mol of the compound (II). This reaction may be carried out using an excess amount of the compound (III) as a base. The reaction temperature is normally −20° to 150° C., preferably about −10° to 100° C.

The quinoline or quinazoline derivative (I) thus obtained can be isolated and purified by conventional separation and purification techniques such as concentration, concentration under reduced pressure, solvent extraction, crystallization, recrystallization, redistribution, chromatography, etc.

The starting compound (II) can be obtained, for example, by the following method.

Method B

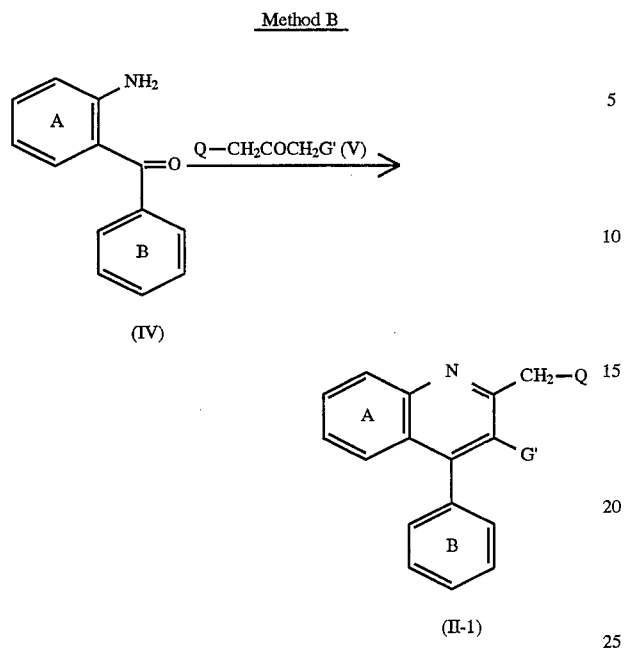

Method C

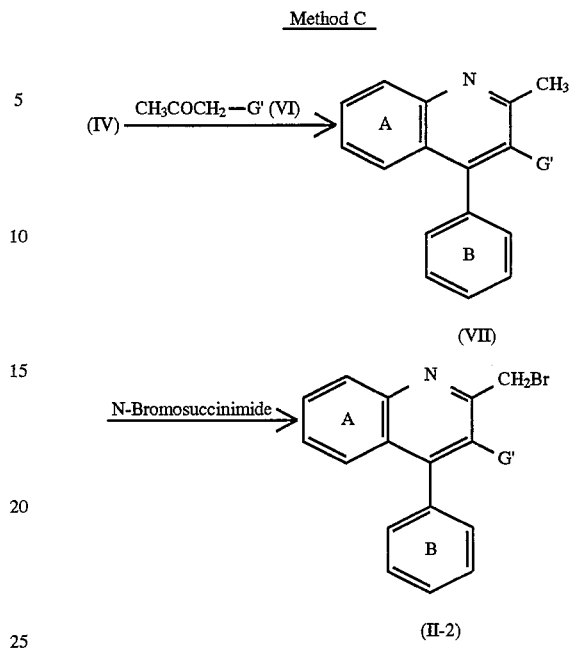

wherein G' is an esterified carboxyl group, and the other symbols are as defined above.

The esterified carboxyl group represented by G' in the formulas (V) and (II-1) includes the esterified carboxyl groups represented by G.

In this method, the 2-aminobenzophenone derivative (IV) is reacted with the compound (V) in the presence of an acid to prepare the compound (II-1). The reaction of the compound (IV) with the compound (V) is carried out in an appropriate solvent. Examples of the solvent include aromatic hydrocarbons (e.g., benzene, toluene, xylene, etc.), ethers (e.g., dioxane, tetrahydrofuran, dimethoxyethane, etc.), N,N-dimethyl formamide, dimethyl sulfoxide, chloroform, dichloromethane, 1,2-dichloroethane, 1,1,2,2-tetrachloroethane, alcohols (e.g., methanol, ethanol, propanol, etc.), acetic acid, etc.

The reaction of the compound (IV) with the compound (V) is carried out in the presence of an appropriate acid such as Lewis acids (e.g., aluminium chloride, zinc chloride, etc.), hydrochloric acid, sulfuric acid, trifluoroacetic acid, etc. The amount of the acid to be used is preferably about 0.05 to 0.5 mol per mol of the compound (IV). The reaction temperature is normally 20° to 200° C., preferably about 30° to 150° C. The reaction time is 0.5 to 20 hours, preferably 1 to 10 hours.

The compound (II-1) thus obtained can be isolated and purified by conventional separation and purification techniques such as concentration, concentration under reduced pressure, solvent extraction, crystallization, recrystallization, redistribution, chromatography, etc.

wherein each symbol is as defined above.

In this method, the 2-aminobenzophenone derivative (IV) is reacted with the acetoacetic acid ester derivative (VI) in the presence of an acid to give the compound (VII). The compound (VII) is then brominated to give the 2-bromomethylquinoline derivative (II-2). The reaction of the compound (IV) with the compound (VI) can be carried out according to the same manner as that of Method B. The compound (VII) is brominated according to a conventional method, for example, by reacting it with N-bromosuccinimide, etc., in an appropriate solvent. Examples of the solvent include halogenated hydrocarbons such as carbon tetrachloride chloroform, dichloromethane, 1,2-dichloroethane, 1,1,2,2,-tetrachloroethane, etc. The amount of N-bromosuccinimide to be used is 1 to 2 mol per mol of the compound (VII).

The bromination is carried out in the presence of a free-radical initiator such as benzoyl peroxide, 2,2'-azobis (isobutyronitrile), etc. The amount of the free-radical initiator to be used is preferably 0.001 to 0.01 mol per mol of the compound (VII). The reaction temperature is normally 20° to 150° C., preferably about 30° to 100° C. The reaction time is 0.5 to 20 hours, preferably 1 to 10 hours.

The compound (II-2) thus obtained can be isolated and purified by conventional separation and purification techniques such as concentration, concentration under reduced pressure, solvent extraction, crystallization, recrystallization, redistribution, chromatography, etc.

Method D

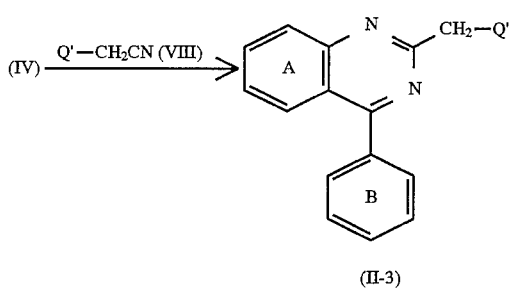

(II-3)

wherein Q' is a halogen atom, and the other symbols are as defined above.

The halogen atom represented by Q' in the formulas (VIII) and (II-3) includes chlorine, bromine, iodine, etc.

In this method, the 2-aminobenzophenone derivative (IV) is reacted with the halogenoacetonitrile derivative (VIII) to give the 2-halogenomethylquinazoline derivative (II-3). The reaction of the compound (IV) with the compound (VIII) can be carried out using an excess amount of the compound (VIII) as a solvent in the presence of an acid. The acid includes acids used in Method B. The amount of the acid to be used is about 1 to 5 mol, preferably 1 to 2 mol, per mol of the compound (IV). The reaction time is normally 0.5 to 30 hours, preferably 1 to 10 hours. The reaction temperature is normally 20° to 200° C., preferably 30° to 150° C.

The quinazoline derivative (II-3) thus obtained can be isolated and purified by conventional separation and purification techniques such as concentration, concentration under reduced pressure, solvent extraction, crystallization, recrystallization, redistribution, chromatography, etc.

Method E

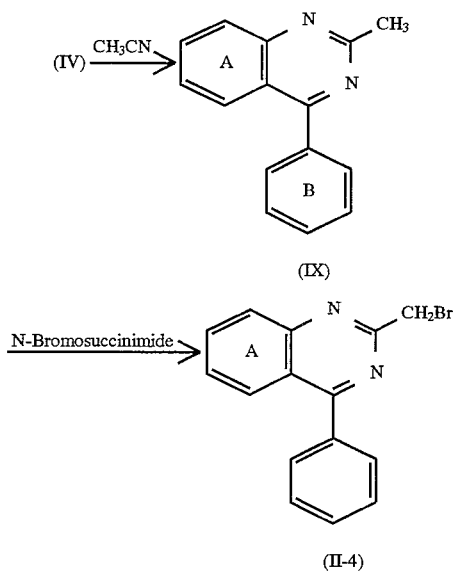

wherein each symbol is as defined above.

In this method, the 2-aminobenzophenone derivative (IV) is reacted with acetonitrile to give the 2-methylquinazoline derivative (IX). The compound (IX) is subjected to bromination to give the 2-bromomethylquinazoline derivative (II-4). The reaction of the compound (IV) with acetonitrile can be carried out according to the same manner as that of Method D. The bromination of the compound (IX) can be carried out according to the same manner as that of the bromination of the compound (VII) in Method C.

The quinazoline derivative (II-4) thus obtained can be isolated and purified by conventional separation and purification techniques such as concentration, concentration under reduced pressure, solvent extraction, crystallization, recrystallization, redistribution, chromatography, etc.

Method F

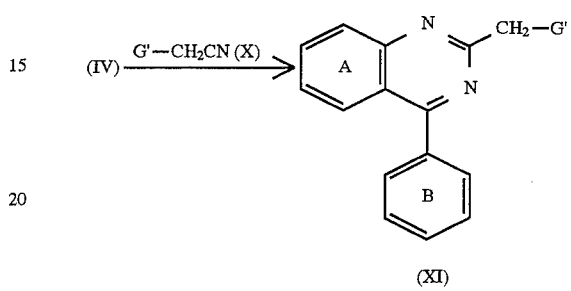

(XI)

wherein each symbol is as defined above.

In this method, the 2-aminobenzophenone derivative (IV) is reacted with the cyanoacetic acid ester derivative (X) to give the quinazoline derivative (XI). The reaction of the compound (IV) with the compound (X) can be carried out according to the same manner as that of Method D.

The quinazoline derivative (XI) thus obtained can be isolated and purified by conventional separation and purification techniques such as concentration, concentration under reduced pressure, solvent extraction, crystallization, recrystallization, redistribution, chromatography, etc.

Method G

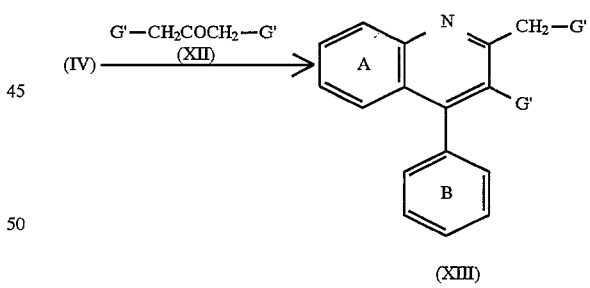

(XIII)

wherein each symbol is as defined above.

In this method, the 2-aminobenzophenone derivative (IV) is reacted with the acetonedicarboxylic acid ester derivative (XII) to give the quinoline derivative (XIII). The reaction of the compound (IV) with the compound (XII) can be carried out according to the same manner as that of Method B.

The quinoline derivative (XIII) thus obtained can be isolated and purified by conventional separation and purification techniques such as concentration, concentration under reduced pressure, solvent extraction, crystallization, recrystallization, redistribution, chromatography, etc.

Method H

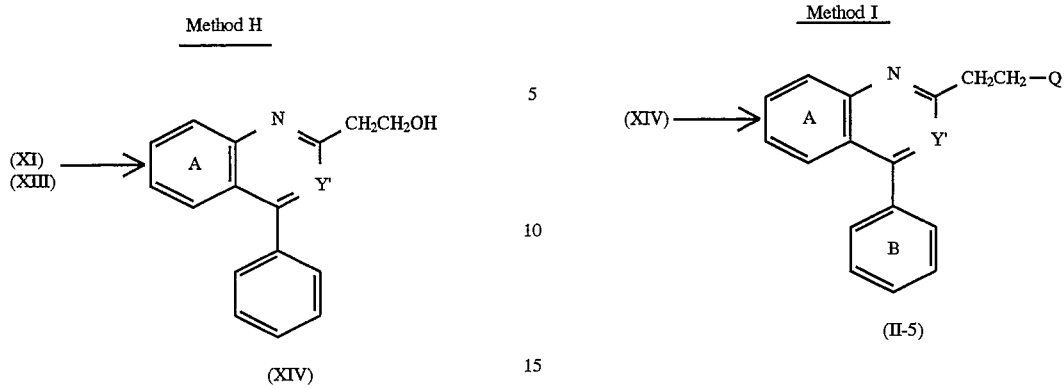

wherein Y' is a nitrogen atom or C—G', and the other symbols are as defined above.

In this method, the compound (XI) or (XIII) obtained by Method F or G is subjected to reduction to give the alcohol (XIV). This reduction can be carried out by per se known methods, for example, by reacting the compound (XI) or (XIII) with a metal hydride, metal hydride complex, diborane or substituted borane, catalytic hydrogenation, etc. That is, this reaction is carried out by treating the compound (XI) or (XIII) with a reducing agent. Examples of the reducing agent include metals and metal salts such as alkaline metal borehydride (e.g., sodium borehydride, lithium borehydride, etc.), metal hydride complexes (e.g., lithium aluminum hydride, etc.), metal hydrides (e.g., sodium hydride, etc.), organic tin compounds (e.g., triphenyltin hydride, etc.), nickel compounds, zinc compounds, etc.; catalytic reducing agents using a transition metal catalyst (e.g., palladium, platinum, rhodium, etc.) and hydrogen; diborane; etc.

This reaction is carried out in an organic solvent which does not have a detrimental effect on the reaction. The solvent is appropriately selected depending upon the kind of the reducing agent. Examples of the solvent include aromatic hydrocarbons (e.g., benzene, toluene, xylene, etc.), halogenated hydrocarbons (e.g., chloroform, carbon tetrachloride, dichloromethane, 1,2-dichloroethane, 1,1,2,2-tetrachloroethane, etc.), ethers (e.g., diethyl ether, tetrahydrofuran, dioxane, etc.), alcohols (e.g., methanol, ethanol, propanol, isopropanol, 2-methoxyethanol, etc.), amides (e.g., N,N-dimethylformamide, etc.), etc. These solvents can be used alone or as a mixture thereof. The reaction temperature is normally −20° to 150° C., preferably about 0° to 100° C. The reaction time is about 1 to 24 hours.

The compound (XIV) thus obtained can be isolated and purified by conventional separation and purification techniques such as concentration, concentration under reduced pressure, solvent extraction, crystallization, recrystallization, redistribution, chromatography, etc.

Method I wherein each symbol is as defined above.

In this method, the compound (XIV) is reacted with a halogenating or sulfonylating agent to give the compound (II-5).

The halogenating agent is preferably thionyl chloride, phosphorus tribromide, etc., which provide the compound of the formula (II-5) wherein Q is chlorine or bromine. This reaction is carried out in an appropriate inert solvent (e.g., benzene, toluene, xylene, chloroform, dichloromethane, etc.) or in excess halogenating agent as a solvent at −10° to 80° C. The amount of the halogenating agent to be used is 1 to 20 mol per mol of the compound (XIV).

The sulfonylating agent is preferably mesyl chloride, tosyl chloride, benzenesulfonyl chloride, etc., which provide the compound of the formula (II-5) wherein Q is mesyloxy, tosyloxy, benzenesulfonyloxy, etc., respectively. This reaction is carried out in an appropriate inert solvent (e.g., benzene, toluene, xylene, ethyl ether, ethyl acetate, tetrahydrofuran, chloroform, dichloromethane, etc.) in the presence of a base (e.g., triethylamine, N-methylmorpholine, sodium bicarbonate, potassium bicarbonate, sodium carbonate, potassium carbonate, etc.) at −10° to 30° C. The amounts of the sulfonylating agent and base to be used are 1 to 1.2 mol per mol of the compound (XIV).

The compound of the formula (II-5) wherein Q is chlorine, bromine or sulfonyloxy thus obtained is reacted with sodium iodide or potassium iodide (1 to 1.5 mol per mol of the compound (II-5)) to give the compound of the formula (II-5) wherein Q is iodine. In this case, the reaction is carried out in a solvent such as acetone, methyl ethyl ketone, methanol, ethanol, etc., at 20° to 80° C.

The compound (II-5) thus obtained can be isolated and purified by conventional separation and purification techniques such as concentration, concentration under reduced pressure, solvent extraction, crystallization, recrystallization, redistribution, chromatography, etc.

Method J (II-1)
(II-2)
(II-3) Oxidation →
(II-4)
(II-5)

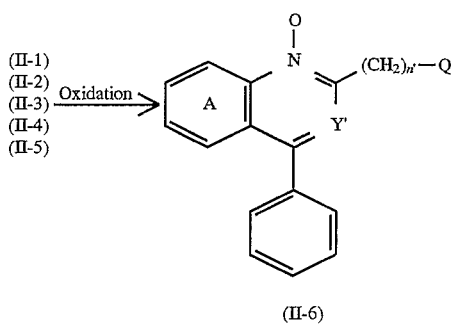

(II-6)

wherein n' is 1 or 2, and the other symbols are as defined above.

In this method, the compound (II-1), (II-2), (II-3), (II-4) or (II-5) obtained in Method B, C, D, E or I, respectively, is oxidized to give the compound (II-6). This oxidation is carried out according to a conventional method using an oxidizing agent such as m-chloroperbenzoic acid, hydrogen peroxide, peresters, sodium metaperiodate, etc. This oxidation is preferably carried out in an organic solvent that is inert in the reaction conditions, such as halogenated hydrocarbons (e.g., methylene chloride, chloroform, dichloroethane, etc.), hydrocarbons (e.g., benzene, toluene, etc.), and alcohols (e.g., methanol, ethanol, propanol, etc.). The amount of the oxidizing agent to be used is 1 to 5 mol, preferably 1 to 3 mol, per mol of the compound (II-1), (II-2), (II-3), (II-4) or (II-5). The reaction temperature is −10° to 150° C. preferably about 0° to 100° C. The reaction time is normally 0.5 to 10 hours.

The quinoline 1-oxide or quinazoline 1-oxide derivative (II-6) thus obtained can be isolated and purified by conventional separation and purification techniques such as concentration, concentration under reduced pressure, solvent extraction, crystallization, recrystallization, redistribution, chromatography, etc.

The quinoline derivative (I-1) included in the compound (I) can also be prepared by Method K.

Method K

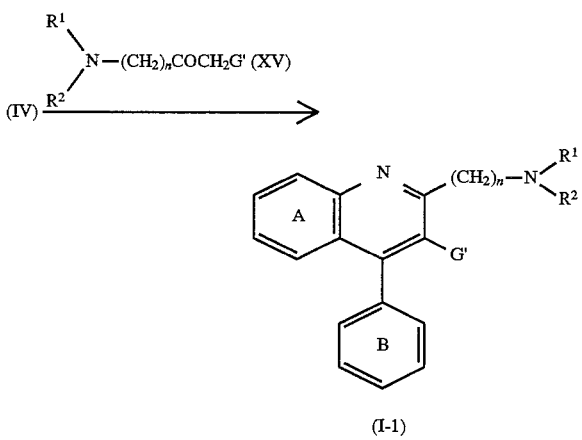

wherein each symbol is as defined above.

In this method, the 2-aminobenzophenone derivative (IV) is reacted with the compound (XV) to give the compound (I-1). This method is carried out according to the same manner as that of Method B.

The quinoline derivative (I-1) thus obtained can be isolated and purified by conventional separation and purification techniques such as concentration, concentration under reduced pressure, solvent extraction, crystallization, recrystallization, redistribution, chromatography, etc.

The quinolinecarboxylic acid derivative (I-3) included in the compound (I) can also be prepared by Method L.

Method L

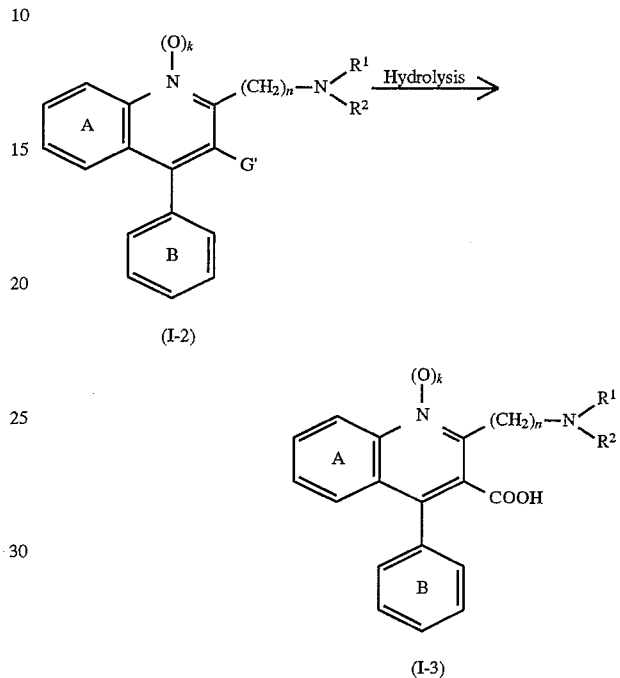

wherein each symbol is as defined above.

In this method, the quinoline-3-carboxylic acid ester derivative (I-2) is subjected to hydrolysis to give the carboxylic acid derivative (I-3).

This hydrolysis is carried out according to a conventional method in water or water-containing solvent in the presence of an acid or base. Examples of the solvent include alcohols (e.g., methanol, ethanol, propanol, 2-methoxyethanol, ethylene glycol, etc.), ethers (e.g., dioxane, tetrahydrofuran, etc.), acetic acid, acetonitrile, acetone, 2-butanone, N,N-dimethylformamide, dimethylsulfoxide, etc. Examples of the acid include hydrochloric acid, sulfuric acid, nitric acid, hydrobromic acid, etc. Examples of the base include sodium hydroxide, potassium hydroxide, barium hydroxide, lithium hydroxide, potassium carbonate, sodium carbonate, etc. Preferably, the acid or base is used in excess based on the compound (I-2) (e.g., base: 1 to 10 mol, acid: 1 to 50 mol, per mol of the compound (I-2)). The reaction temperature is normally at −20° to 150° C., preferably −10° to 100° C. The reaction time is 1 to 50 hours.

The quinoline derivative (I-3) thus obtained can be isolated and purified by conventional separation and purification techniques such as concentration, concentration under reduced pressure, solvent extraction, crystallization, recrystallization, redistribution, chromatography, etc.

The compound of the formula (I) or a salt thereof used in the present invention has anti-inflammatory activity, and antipyretic and analgesic activity. In addition, it has been confirmed that the compound of the formula (I) or a salt thereof has potent antiarthritic activity in an experimental model with adjuvant arthritis in which similar symptoms to those of human rheumatoid arthritis develop. Further, the compound used in the present invention has low toxicity. For example, when the compound prepared in Example 5 was orally administered to mice and rats in a dose of 250 mg/kg, no mice or rats died. When the compound prepared in Example 54 was orally administered to rats in a dose of 500 mg/kg, no rats died. Thus, the compound (I) used in the present invention is applicable to all arthritis exhibiting inflammatory symptoms in joints of mammals such as humans, mice, rats, cats, dogs, rabbits, bovines and swines.

The dose of the compound (I) used in the present invention can appropriately be selected depending upon the administration route and condition of the patient to be treated. Normally, the dose can be selected from the regions of 5 mg to 1000 mg per adult in the case of oral administration, and 1 mg to 100 mg per adult in the case of parenteral administration. The compound in the above dose can be administered daily in one to three divided portions.

The following experiment illustrates the pharmacological activity of the compound (I) or its salt used in the present invention.

EXPERIMENT 1

Effects on rat adjuvant arthritis

Male Lewis rats (7 weeks old, Charles River Japan Inc.) were sensitized by injecting Freund's complete adjuvant (a 0.5% suspension of killed tubercle bacilli in liquid paraffin) (0.05 ml) intradermally into a plantar part of a right hind leg. A test drug (12.5 mg/kg) was suspended in 0.5% methylcellulose, and orally administered once a day for 14 days. The administration was started just before the sensitization (Day 0). The left hind leg volume and the body weight were measured just before the sensitization (Day 0) and on the 14th day, and the plantar edema inhibitory rate (%) and the body weight gain rate (%) based on those of non-sensitized rat groups were calculated.

The results are indicated in each group's mean (N=6) ±S.E., and assessed by Dunnett's test. The risk rate of less than 5% was evaluated as significant. As shown in Table 1, the compound (I) used in the present invention was effective in improving systemic symptoms observed as plantar edema inhibition and body weight gains.

TABLE 1

| Compound | Edema inhibitory rate (%) | Body weight gain rate[1] (%) |
|---|---|---|
| 5 | 103 ** | 16 |
| 18 | 79 ** | 19 |
| 23 | 82 ** | 25 |
| 54 | 83 ** | 18 |

[1] $\frac{\text{(Drug administered rats)} - \text{(Sensitized control rats)}}{\text{(Normal control rats)} - \text{(Sensitized control rats)}} \times 100$

**; $p < 0.01$, *; $p < 0.05$

As described above, the present invention provides an anti-inflammatory pharmaceutical composition comprising a quinoline or quinazoine derivative. The pharmaceutical composition of the present invention is significantly effective particularly against arthritis, and has low toxicity and can be administered safely. Further, the present invention provides a novel quinoline or quinazoline derivative having anti-inflammatory activity.

The following Examples (Ex.) and Reference examples (Ref.) further illustrate the present invention in detail but are not to be construed to limit the scope thereof.

REFERENCE EXAMPLE 1

Conc. sulfuric acid (0.3 ml) was added to a mixture of 2-amino-4,5-ethylenedioxy-3',4'-dimethoxybenzophenone (6.5 g), ethyl 4-chloroacetoacetate (3.7 g) and acetic acid (60 ml), and the mixture was stirred at 100° C. for 3 hours. The reaction mixture was concentrated under reduced pressure. The residue was poured into water and made alkaline with 2N sodium hydroxide, and extracted with chloroform. The chloroform layer was washed with water and dried over magnesium sulfate, and the solvent was evaporated under reduced pressure. The residue was subjected to column chromatography on silica gel. The fractions eluted with chloroform-ethyl acetate (7:3, v/v) gave ethyl 2-chloromethyl-6,7-ethylenedioxy-4-(3,4-dimethoxyphenyl)quinoline-3-carboxylate (5.5 g, 60%). This compound was recrystallized from acetone. Colorless prisms, mp. 197°–198° C.

REFERENCE EXAMPLES 2 TO 7

According to the same manner as in Reference Example 1, the compounds in Table 2 were obtained.

TABLE 2

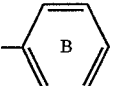

| Ref. No. | A¹, A² | B | Yield (%) | mp (°C.) | Recrystallization solvent |
|---|---|---|---|---|---|
| 2 | 6,7-(CH$_3$O)$_2$ | 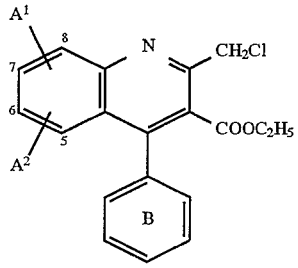 | 53 | 147–148 | Acetone-Ether |
| 3 | 6,7-(CH$_3$O)$_2$ | 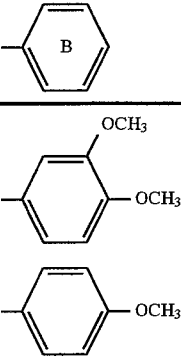 | 48 | 108–109 | Ether |
| 4 | 6,7-(CH$_3$O)$_2$ | 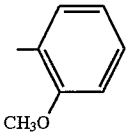 | 53 | 146–147 | Ethyl acetate-Hexane |
| 5 | 6,7-(C$_2$H$_5$O)$_2$ | 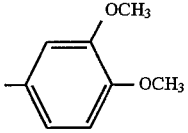 | 68 | 124–125 | Ethyl acetate-Hexane |
| 6 | 6-Cl, H | 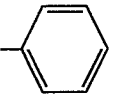 | 61 | 105–106 | Methanol-H$_2$O |
| 7 | 6,7-(CH$_3$O)$_2$ | 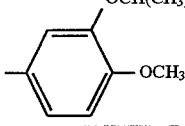 | 50 | 126–127 | Ethanol |

REFERENCE EXAMPLE 8

Conc. sulfuric acid was added to a mixture of 2-amino-4,5,3',4'-tetramethoxybenzophenone, ethyl acetoacetate and acetic acid. The mixture was treated according to the same manner as in Reference Example 1 to give ethyl 4-(3,4-dimethoxyphenyl)-6,7-dimethoxy-2-methylquinoline-3-carboxylate (83%). This compound was recrystallized from ethanol. Colorless prisms, mp. 147°–148° C.

REFERENCE EXAMPLE 9

A mixture of ethyl 4-(3,4-dimethoxyphenyl)-6,7-dimethoxy-2-methylquinoline-3-carboxylate (411 mg), N-bromosuccinimide (214 mg), 2,2'-azobis(isobutyronitrile) (10 mg) and carbon tetrachloride (10 ml) was stirred under reflux for 5 hours. The reaction mixture was washed with water and dried over magnesium sulfate, and the solvent was evaporated under reduced pressure. The residue was subjected to column chromatography on silica gel. The fractions eluted with chloroform-ethyl acetate (10:1, v/v) gave ethyl 2-bromomethyl-6,7-dimethoxy-4-(3,4-dimethoxyphenyl) quinoline-3-carboxylate (285 mg, 58%). This compound was recrystallized from ethyl acetate-hexane. Colorless prisms, mp. 135°–136° C.

REFERENCE EXAMPLE 10

Conc. sulfuric acid was added to a mixture of 2-amino-4,5,3',4'-tetramethoxybenzophenone, propylacetoacetate and acetic acid. The mixture was treated according to the same manner as in Reference Example 1 to give propyl 4-(3,4-dimethoxyphenyl)-6,7-dimethoxy-2-methylquinoline-3-carboxylate (79%). This compound was recrystallized from ethyl acetateisopropyl ether. Colorless prisms, mp. 153°–155° C.

REFERENCE EXAMPLE 11

Conc. sulfuric acid was added to a mixture of 2-amino-4,5,3',4'-tetramethoxybenzophenone, butyl acetoacetate and acetic acid. The mixture was treated according to the same manner as in Reference Example 1 to give butyl 4-(3,4-dimethoxyphenyl)-6,7-dimethoxy-2-methylquinoline-3-carboxylate (53%). This compound was recrystallized from ethyl acetatehexane. Colorless prisms, mp. 119°–120° C.

REFERENCE EXAMPLE 12

According to the same manner as in Reference Example 9, propyl 2-bromomethyl-4-(3,4-dimethoxyphenyl)-6,7-dimethoxyquinoline-3-carboxylate (48%) was obtained and recrystallized from ethyl acetate-isopropyl ether. Colorless prisms, mp. 144°–145° C.

REFERENCE EXAMPLE 13

According to the same manner as in Reference Example 9, butyl 2-bromomethyl-4-(3,4-dimethoxyphenyl)-6,7-dimethoxyquinoline-3-carboxylate ( 56% ) was obtained and recrystallized from ethyl acetate-ether. Colorless prisms, mp. 160°–161° C.

REFERENCE EXAMPLE 14

Aluminium chloride powder (6.7 g) was added to a mixture of 2-amino-4,5,3',4'-tetramethoxybenzophenone (8.0 g) and chloroacetonitrile (25 ml), and the mixture was stirred at 100° C. for 2 hours. The reaction mixture was poured into water and extracted with chloroform. The chloroform layer was washed with water and dried over magnesium sulfate. The residue was subjected to column chromatography on silica gel. The fractions eluted with chloroform-ethyl acetate (10:1, v/v) gave 2-chloromethyl-4-(3,4-dimethoxyphenyl)-6,7-dimethoxyquinazoline (4.9 g, 52%). This compound was recrystallized from acetone. Colorless prisms, mp. 183°–184° C.

REFERENCE EXAMPLE 15

Aluminium chloride powder (5.3 g) was added to a mixture of 2-amino-4,5,3',4'-tetramethoxybenzophenone (6.3 g) and methyl cyanoacetate (23 ml), and the mixture was stirred at 100° C. for 2.5 hours. The reaction mixture was poured into water and extracted with chloroform. The chloroform layer was washed with water and dried over magnesium sulfate. The residue was subjected to column chromatography on silica gel. The fractions eluted with hexane-ethyl acetate (4:1, v/v) gave methyl 4-(3,4-dimethoxyphenyl)-6,7-dimethoxyquinazoline-2-acetate. This compound was recrystallized from acetone. Colorless needles, mp. 152°–153° C.

REFERENCE EXAMPLE 16

Methanol (15 ml) was added dropwise to a mixture of methyl 4-(3,4-dimethoxyphenyl)-6,7-dimethoxyquinazoline-2-acetate (4.0 g), sodium borohydride (1.9 g) and tetrahydrofuran (80 ml) under reflux. The mixture was stirred under reflux for 2 hours, and then poured into water, and extracted with ethyl acetate. The ethyl acetate layer was washed with water and dried over magnesium sulfate. Evaporation of the solvent gave 4-(3,4-dimethoxyphenyl)-2-(2-hydroxyethyl)-6,7-dimethoxyquinazoline (3.0 g, 81%). This was recrystallized from ethyl acetate. Colorless needles, mp. 165°–166° C.

REFERENCE EXAMPLE 17

Phosphorus tribromide (PBr$_3$)(0.95 g) was added dropwise to a solution of 4-(3,4-dimethoxyphenyl)-2-(2-hydroxyethyl)-6,7-dimethoxyquinazoline (2.6 g) in benzene (50 ml) at room temperature. The mixture was stirred at 75° C. for 1 hour, poured into ice-cold water, neutralized with an aqueous saturated solution of sodium bicarbonate, and then extracted with chloroform. The chloroform layer was washed with water, dried over magnesium sulfate, and the solvent was evaporated. The residue was subjected to column chromatography on silica gel. The fractions eluted with chloroform-ethyl acetate (3:1, v/v) gave 2-(2-bromoethyl)-4-(3,4-dimethoxyphenyl)-6,7-dimethoxyquinazoline (1.1 g, 37%). This was recrystallized from ethyl acetate. Colorless needles, mp. 166°–167° C.

REFERENCE EXAMPLE 18

According to the same manner as in Reference Example 1, ethyl 6-chloro-2-chloromethyl-4-(4-chlorophenyl)quinoline-3-carboxylate was obtained and recrystallized from ethyl acetate-hexane. Colorless prisms, mp. 140°–141° C.

REFERENCE EXAMPLE 19

According to the same manner as in Reference Example 1, ethyl 2-chloromethyl-4-(4-chlorophenyl)-6,7-dimethoxyquinoline-3-carboxylate was obtained and recrystallized from ethanol. Colorless prisms, mp. 153°–154° C.

REFERENCE EXAMPLE 20

According to the same manner as in Reference Example 1, ethyl 2-chloromethyl-4-(4-fluorophenyl)-6,7-dimethoxyquinoline-3-carboxylate was obtained and recrystallized from ethanol. Colorless prisms, mp. 147°–148° C.

REFERENCE EXAMPLE 21

According to the same manner as in Reference Example 1, ethyl 2-chloromethyl-4-(3,4-dichlorophenyl)-6,7-dimethoxyquinoline-3-carboxylate was obtained and recrystallized from ethyl acetate-hexane. Colorless prisms, mp. 159°–160° C.

REFERENCE EXAMPLE 22

A mixture of ethyl 2-chloromethyl-4-(3,4-dimethoxyphenyl)-6,7-dimethoxyquinoline-3-carboxylate (3.0 g), m-chloroperbenzoic acid (85%, 2.3 g) and methanol (40 ml) was stirred under reflux for 2 hours. The reaction mixture was concentrated under reduced pressure. The residue was dissolved in chloroform. The chloroform layer was washed with water and dried over magnesium sulfate, and the solvent was evaporated under reduced pressure. The residue was subjected to column chromatography on silica gel. The fractions eluted with chloroform-ethyl acetate (6:4, v/v) gave ethyl 2-chloromethyl-4-(3,4-dimethoxyphenyl)-6,7-dimethoxyquinoline-3-carboxylate 1-oxide (2.0 g, 65%). This was recrystallized from acetone-isopropyl ether. Colorless prisms, mp. 193°–194° C.

REFERENCE EXAMPLE 23

Conc. sulfuric acid (1.5 ml) was added to a mixture of 2-amino-4,5,3',4'-tetramethoxybenzophenone (50.0 g), diethyl acetonedicarboxylate (35.0 g) and acetic acid (400 ml), and the mixture was stirred at 100° C. for 2.5 hours. The reaction mixture was concentrated under reduced pressure. The residue was poured into water, neutralized with an aqueous saturated solution of sodium bicarbonate, and extracted with chloroform. The chloroform layer was washed with water and dried over magnesium sulfate, and the solvent was evaporated under reduced pressure. The residual crystals were recrystallized from acetone to give ethyl 4-(3,4-dimethoxyphenyl)-6,7-dimethoxy-3-ethoxycarbonylquinoline-2-acetate (48.8 g, 64%). Colorless prisms, mp. 146°–147° C.

REFERENCE EXAMPLE 24

A solution of ethyl 4-(3,4-dimethoxyphenyl)-6,7-dimethoxy-3-ethoxycarbonylquinoline-2-acetate (5.8 g) in tetrahydrofuran (100 ml) was added dropwise to a suspension of lithium aluminum hydride (0.455 g) in tetrahydrofuran (50 ml) at 0° C. The mixture was stirred at 0° C. for 1 hour, and then water (2.5 ml) was added dropwise, and the mixture was stirred for 30 minutes. The insoluble solids were separated by filtration, and the filtrate was concentrated under reduced pressure. The residue was subjected to column chromatography on silica gel. The fractions eluted with chloroform-ethyl acetate (1:1, v/v) gave ethyl 4-(3,4-dimethoxyphenyl)-2-(2-hydroxyethyl)-6,7-dimethoxyquinoline-3-carboxylate (1.75 g, 33%). This was recrystallized from ethyl acetate-hexane. Colorless prisms, mp. 150°–151° C.

REFERENCE EXAMPLE 25

Phosphorus tribromide (1.0 g) was added dropwise to a solution of ethyl 4-(3,4-dimethoxyphenyl)-2-(2-hydroxyethyl)-6,7-dimethoxyquinoline-3-carboxylate (1.7 g) in benzene (50 ml) at room temperature. The mixture was stirred at 80° C. for 1 hour, poured into ice-cold water, neutralized with an aqueous saturated solution of sodium bicarbonate, and then extracted with chloroform. The chloroform layer was washed with water, dried over magnesium sulfate, and the solvent was evaporated under reduced pressure. The residue was subjected to column chromatography on silica gel. The fractions eluted with chloroform-ethyl acetate (1:1, v/v) gave ethyl 2-(2-bromoethyl)-4-(3,4-dimethoxyphenyl)-6,7-dimethoxyquinoline-3-carboxylate (0.49 g, 26%). This was recrystallized from ethyl acetate-hexane. Colorless prisms, mp. 132°–133° C.

REFERENCE EXAMPLE 26

A mixture of benzyl 4-bromobutanoate (58.6 diethylamine (58.3 g) and dichloromethane (1000 ml) was stirred under reflux for 14 hours. The reaction mixture was washed with water and dried over magnesium sulfate, and the solvent was evaporated under reduced pressure. The residue was subjected to column chromatography on silica gel. The fractions eluted with ethyl acetate gave benzyl 4-(N,N-diethylamino)butanoate (33.8 g, 60%).

NMR (δ ppm in $CDCl_3$): 0.99 (6H,t,J=7.2 Hz), 1.78 (2H,quintet,J=7.2 Hz), 2.39 (2H,t,J=7.2 Hz), 2.49 (4H,q,J=7.2 Hz), 5.11 (2H,s), 7.30–7.41 (5H,m).

REFERENCE EXAMPLE 27

According to the same manner as in Reference Example 26, benzyl 5-(N,N-diethylamino)pentanoate was obtained.

NMR (δ ppm in $CDCl_3$): 0.99 (6H,t,J=7.0 Hz), 1.40–1.78 (4H,m), 2.33–2.50 (4H,m), 2.49 (4H,q,J=7.0 Hz), 5.11 (2H, s), 7.30–7.40 (5H,m).

REFERENCE EXAMPLE 28

A mixture of benzyl 4-(N,N-diethylamino)butanoate (33.8 g), palladium-carbon (5%, 7 g) and ethanol (500 ml) was subjected to catalytic hydrogenation at room temperature and 1 atm. The catalyst was filtered off, and the filtrate was concentrated under reduced pressure to give 4-(N,N-diethylamino)butanoic acid (16.2 g, 75%). mp. 45°–47° C.

NMR (δ ppm in $CDCl_3$): 1.30 (6H,t,J=6.6 Hz), 1.92 (2H,quintet,J=6.6 Hz), 2.52 (2H,t,J=6.6 Hz), 2.95 (2H,t,J=6.6 Hz), 2.99 (4H,q,J=6.6 Hz).

REFERENCE EXAMPLE 29

According to the same manner as in Reference Example 28, 5-(N,N-diethylamino)pentanoic acid was obtained.

NMR (δ ppm in $CDCl_3$): 1.26 (6H,t,J=7.2 Hz), 1.53–1.85 (4H,m), 2.29 (2H,t,J=6.0 Hz), 2.90 (2H,t,J=6.0 Hz), 3.06 (4H,q,J=6.0 Hz).

REFERENCE EXAMPLE 30

N,N'-Carbonyldiimidazole (11.2 g) was added to a suspension of 4-(N,N-diethylamino)butanoic acid (10.0 g) in tetrahydrofuran (400 ml), and the mixture was stirred at room temperature for 6 hours. Then monoethyl malonate magnesium salt ($Mg(OCOCH_2COOC_2H_5)_2$)(19.8 g) was added, and the mixture was stirred at room temperature for 14 hours. The reaction mixture was concentrated under reduced pressure, and the residue was dissolved in chloroform. The chloroform layer was washed with water and dried over magnesium sulfate, and the solvent was evaporated under reduced pressure. The residue was subjected to column chromatography on silica gel. The fractions eluted with chloroform-methanol (5:1, v/v) gave ethyl 6-(N,N-diethylamino)-3-oxohexanoate (7.6 g, 53%).

NMR (δ ppm in $CDCl_3$): 1.00 (6H,t,J=7.0 Hz), 1.28 (3H,t,J=7.2 Hz), 1.75 (2H,quintet,J=7.2 Hz), 2.36–2.64 (8H, m), 3.46 (2H,broad s), 4.19 (2H,q,J=7.2 Hz).

REFERENCE EXAMPLE 31

According to the same manner as that described in Reference Example 30, ethyl 7-(N,N-diethylamino)-3-oxoheptanoate was obtained.

NMR (δ ppm in $CDCl_3$): 1.01 (6H,t,J=7.0 Hz), 1.28 (3H,t,J=7.2 Hz), 1.38–1.70 (4H,m), 2.36–2.60 (8H,m), 3.43 (2H,s), 4.19 (2H,q,j=7.2 Hz).

EXAMPLE 1

Oily sodium hydride (60%, 0.27 g) was added to a solution of morpholine (0.537 g) in N,N-dimethylformamide (20 ml), and the mixture was stirred at room temperature for 15 minutes. Then ethyl 2-chloromethyl-4-(3,4-dimethoxyphenyl)-6,7-dimethoxyquinoline-3-carboxylate (2.5 g) was added. The mixture was stirred at 100° C. for 2 hours, poured into water and extracted with ethyl acetate. The ethyl acetate layer was washed with water and dried over magnesium sulfate, and the solvent was evaporated. The residual crystals were separated by filtration, and then recrystallized from ethanol to give ethyl 4-(3,4-dimethoxyphenyl)-6,7-dimethoxy-2-morpholinomethylquinoline-3-carboxylate (1.9 g, 68%). Colorless prisms, mp. 146°–147° C.

EXAMPLE 2

A mixture of ethyl 2-chloromethyl-4-(3,4-dimethoxyphenyl)-6,7-dimethoxyquinoline-3-carboxylate (1.0 g), piperazine (1.15 g) and methanol (15 ml) was stirred at room temperature for 36 hours. The reaction mixture was concentrated under reduced pressure. 6N hydrochloric acid (30 ml) was added to the residue, and the mixture was washed with dichloromethane. The aqueous layer was neutralized with 2N sodium hydroxide, and extracted with dichloromethane. The dichloromethane layer was washed with water and dried over magnesium sulfate, and the solvent was evaporated. The residual crystals were separated by filtration, and then recrystallized from dichloromethane-hexane to give ethyl 4-(3,4-dimethoxyphenyl)-6,7-dimethoxy-2-piperazinomethylquinoline-3-carboxylate (0.43 g, 39%). Colorless prisms, mp. 192°–193° C.

EXAMPLE 3

Oily sodium hydride (60%, 0.753 g) was added to a solution of thiomorpholine (1.8 g) in N,N-dimethylformamide (50 ml), and the mixture was stirred at room temperature for 15 minutes. Then ethyl 2-chloromethyl-4-(3,4-dimethoxyphenyl)-6,7-dimethoxyquinoline-3-carboxylate (6.0 g) was added. The mixture was stirred at room temperature overnight, poured into water and extracted with ethyl acetate. The ethyl acetate layer was washed with water and dried over magnesium sulfate, and the solvent was evaporated. The residue was subjected to column chromatography on silica gel. The fractions eluted with chloroform-ethyl acetate (7:3, v/v) gave ethyl 4-(3,4-dimethoxyphenyl)-6,7-dimethoxy-2-thiomorpholinomethylquinoline-3-carboxylate (1.4 g, 42%). This compound was recrystallized from ethanol. Colorless prisms, mp. 148°–149° C.

EXAMPLE 4

Oily sodium hydride (60%, 0.466 g) was added to a solution of N-methylhomopiperazine (1.23 g) in N,N-dimethylformamide (40 ml), and the mixture was stirred at room temperature for 15 minutes. Then ethyl 2-chloromethyl-4-(3,4-dimethoxyphenyl)-6,7-dimethoxyquinoline-3-carboxylate (4.0 g) was added. The mixture was stirred at 100° C. for 3.5 hours, poured into water and extracted with ethyl acetate. The ethyl acetate layer was washed with water and dried over magnesium sulfate, and the solvent was evaporated. The residue was subjected to column chromatography on silica gel. The fractions eluted with chloroform-methanol (5:1, v/v) gave ethyl 4-(3,4-dimethoxyphenyl)-6,7-dimethoxy-2-[(4-methylhomopiperazino)methyl]quinoline-3-carboxylate (1.0 g, 22%). This compound was recrystallized from ethyl acetatehexane. Colorless prisms, mp. 157°–159° C.

EXAMPLE 5

A mixture of ethyl 2-chloromethyl-4-(3,4-dimethoxyphenyl)-6,7-dimethoxyquinoline-3-carboxylate (4.0 g), diethylamine (1.28 g) and methanol (45 ml) was stirred at room temperature for 4 days. The reaction mixture was poured into water and extracted with dichloromethane. The dichloromethane layer was washed with water and dried over magnesium sulfate, and the solvent was evaporated. The residue was subjected to column chromatography on silica gel. The fractions eluted with ethyl acetate gave ethyl 2-(N,N-diethylaminomethyl)-4-(3,4-dimethoxyphenyl)-6,7-dimethoxyquinoline-3-carboxylate (0.51 g, 18%). This compound was recrystallized from ethyl acetate-hexane. Colorless prisms, mp. 130°–131° C.

EXAMPLE 6

A mixture of ethyl 2-chloromethyl-6,7-dimethoxy-4-(4-methoxyphenyl)quinoline-3-carboxylate (2.0 g), morpholine (2.5 g) and methanol (30 ml) was stirred at room temperature for 17 hours. The reaction mixture was concentrated under reduced pressure, and dichloromethane was added to the residue. The mixture was washed with water and dried over magnesium sulfate, and the solvent was evaporated. The resulting crystals were separated by filtration and recrystallized from ethanol to give ethyl 6,7-dimethoxy-4-(4-methoxyphenyl)-2-morpholinomethylquinoline-3-carboxylate (1.65 g, 74%). Colorless prisms, mp. 165°–166° C.

EXAMPLE 7

According to the same manner as that described in Example 6, ethyl 6,7-dimethoxy-4-(4-methoxyphenyl)-2-piperidinomethylquinoline-3-carboxylate was obtained and recrystallized from ethanol. Colorless prisms, mp. 129°–130° C.

EXAMPLE 8

A mixture of ethyl 2-chloromethyl-6,7-dimethoxy-4-(2-methoxyphenyl)quinoline-3-carboxylate (1.0 g), morpholine (1.25 g) and ethanol (13 ml) was stirred at room temperature for 3 days. The precipitated crystals were separated by filtration and recrystallized from ethyl acetate-hexane to give ethyl 6,7-dimethoxy-4-(2-methoxyphenyl)-2-morpholinomethylquinoline-3-carboxylate (0.76 g, 68%). Colorless prisms, mp. 153°–154° C.

EXAMPLE 9

According to the same manner as that described in Example 6, ethyl 4-(3,4-dimethoxyphenyl)-6,7-ethylenedioxy-2-morpholinomethylquinoline-3-carboxylate was obtained and recrystallized from ethanol. Colorless needles, mp. 174°–175° C.

EXAMPLE 10

According to the same manner as that described in Example 6, ethyl 4-(3,4-dimethoxyphenyl)-6,7-ethylenedioxy-2-piperidinomethylquinoline-3-carboxylate was obtained and recrystallized from ethanol. Colorless prisms, mp. 158°–160° C.

EXAMPLE 11

According to the same manner as that described in Example 6, ethyl 4-(3,4-dimethoxyphenyl)-6,7-diethoxy-2-morpholinomethylquinoline-3-carboxylate was obtained and recrystallized from ethanol. Colorless prisms, mp. 147°–148° C.

EXAMPLE 12

According to the same manner as that described in Example 6, ethyl 4-(3,4-dimethoxyphenyl)-6,7-diethoxy-2-piperidinomethylquinoline-3-carboxylate was obtained and recrystallized from ethanol. Colorless prisms, mp. 154°–155° C.

EXAMPLE 13

According to the same manner as that described in Example 6, ethyl 6-chloro-2-morpholinomethyl-4-phenylquinoline-3-carboxylate was obtained and recrystallized from ethanol. Colorless prisms, mp. 161°–163° C.

EXAMPLE 14

A mixture of ethyl 2-chloromethyl-4-(3-isopropoxy-4-methoxyphenyl)-6,7-dimethoxyquinoline-3-carboxylate (3.0 g), morpholine (2.76 g) and ethanol (50 ml)—dichloromethane (5 ml) was stirred at room temperature overnight. The reaction mixture was concentrated under reduced pressure, and dichloromethane (50 ml) was added to the residue. The dichloromethane layer was washed with water and dried over magnesium sulfate, and the solvent was evaporated. The residue was subjected to column chromatography on silica gel. The fractions eluted with chloroform-ethyl acetate (1:1, v/v) gave ethyl 4-(3-isopropoxy-4-methoxyphenyl)-6,7-dimethoxy-2-morpholinomethylquinoline-3-carboxylate as an oil. This oil was dissolved in ethanol (20 ml), and a solution of hydrogen chloride in ethanol (23%, 1.05 g) was added. The mixture was stirred at room temperature for 10 minutes, and the solvent was evaporated under reduced pressure. The crystals were separated by filtration and recrystallized from ethanol-ether to give ethyl 4-(3-isopropoxy-4-methoxyphenyl)-6,7-dimethoxy-2-morpholinomethylquinoline-3-carboxylate hydrochloride (1.62 g, 45%). Colorless crystals, mp. 185°–188° C.

Elemental Analysis: Calcd. for $C_{29}H_{37}N_2O_7Cl \cdot H_2O$: C,60.15; H,6.79; N,4.84 Found: C,60.51; H,6.58; N,4.73

EXAMPLE 15

According to the same manner as that described in Example 14, ethyl 4-(3-isopropoxy-4-methoxyphenyl)-6,7-dimethoxy- 2-piperidinomethylquinoline-3-carboxylate hydrochloride was obtained and recrystallized from ethanolether. Colorless crystals, mp. 207°–210° C.

Elemental Analysis: Calcd. for $C_{30}H_{39}N_2O_6Cl \cdot \frac{1}{2}H_2O$: C,63.43; H,7.10; N,4.93 Found: C,63.15; H,7.02; N,4.80

EXAMPLE 16

According to the same manner as that described in Example 14, ethyl 2-(N,N-dipentylaminomethyl)-4-(3,4-dimethoxyphenyl)-6,7-dimethoxyquinoline-3-carboxylate dihydrochloride was obtained and recrystallized from dichloromethane - ethyl acetate. Yellow powder, mp. 93°–95° C.

Elemental Analysis: Calcd. for $C_{33}H_{48}N_2O_6Cl_2 \cdot 3/2H_2O$: C,59.45; H,7.71; N,4.20 Found: C,59.58; H,7.88; N,4.14

EXAMPLE 17

According to the same manner as that described in Example 1, ethyl 4-(3,4-dimethoxyphenyl)-6,7-dimethoxy-2-piperidinomethylquinoline-3-carboxylate was obtained and recrystallized from ethanol. Colorless prisms, mp. 148°–149° C.

EXAMPLE 18

According to the same manner as that described in Example 1, ethyl 4-(3,4-dimethoxyphenyl)-6,7-dimethoxy-2-pyrrolidinomethylquinoline- 3-carboxylate was obtained and recrystallized from ethyl acetate - hexane. Colorless prisms, mp. 139°–140° C.

EXAMPLE 19

A mixture of propyl 2-bromomethyl-4-(3,4-dimethoxyphenyl)-6,7-dimethoxyquinoline-3-carboxylate (1.5 g), piperidine (1.27 g) and dichloromethane (30 ml) was stirred at room temperature for 2 days. The reaction mixture was washed with water and dried over magnesium sulfate, and the solvent was evaporated. The residue was subjected to column chromatography on silica gel. The fractions eluted with chloroform-ethyl acetate (10:1, v/v) gave propyl 4-(3,4-dimethoxyphenyl)-6,7-dimethoxy-2-piperidinomethylquinoline-3-carboxylate (0.8 g, 53%). This compound was recrystallized from ethyl acetate - hexane. Colorless prisms, mp. 129°–131° C.

EXAMPLE 20

According to the same manner as that described in Example 19, butyl 4-(3,4-dimethoxyphenyl)-6,7-dimethoxy-2-piperidinomethylquinoline-3-carboxylate was obtained and recrystallized from ethyl acetate - hexane. Colorless needles, mp. 154°–155° C.

EXAMPLES 21 TO 28

According to the same manner as that described in Example 5, the compounds in Table 3 were obtained.

TABLE 3

| Ex. No. | $A^1$, $A^2$ | R | Yield (%) | mp (°C.) | Recrystallization solvent |
|---|---|---|---|---|---|
| 21 | 6,7-$(CH_3O)_2$ | $CH_3$ | 65 | 137–138 | Ethyl acetate-Hexane |
| 22 | 6,7-$(CH_3O)_2$ | $C_3H_7$ | 47 | 92–93 | Ethanol-Hexane |
| 23 | 6,7-$(CH_3O)_2$ | $C_4H_9$ | 50 | 90–92 | Ethanol-Hexane |
| 24 | 6,7-$(CH_3O)_2$ | $(CH_3)_2CH$ | 20 | 134–135 | Ethanol-Hexane |
| 25 | 6,7-$(CH_3O)_2$ | $HOCH_2CH_2$ | 66 | 117–119[1) | Ethyl acetate-Hexane |
| 26 | 6,7-$(CH_3O)_2$ | cyclohexyl | 14 | 174–175[2) | Ethyl acetate-Hexane |
| 27 | 6,7-$(CH_3O)_2$ | $C_6H_5CH_2$ | 36 | 56–58[3) | |
| 28 | 6,7-$(C_2H_5O)_2$ | $C_2H_5$ | 44 | 86–88 | Ethyl acetate-Hexane |

[1) ½ Hydrate.
[2) ¼ Hydrate.
[3) Amorphous solid. NMR(δppm in CDCl₃): 0.97(3H, t, J=7Hz), 3.59(4H, s), 3.78(3H, s), 3.88(3H, s), 3.97(3H, s), 3.99(2H, q, J=7Hz), 4.04(3H, s), 4.13(2H, s), 6.84–7.02(4H, m), 7.10–7.40(10H, m), 7.42(1H, s).

EXAMPLE 29

A mixture of 2-chloromethyl-4-(3,4-dimethoxyphenyl)-6,7-dimethoxyquinazoline (2.0 g), piperidine (2.27 g) and ethanol (40 ml)—dichloromethane (10 ml) was stirred at room temperature for 3 days. The reaction mixture was concentrated under reduced pressure, and dichloromethane (50 ml) was added to the residue. The dichloromethane layer was washed with water and dried over magnesium sulfate, and the solvent was evaporated. The residue was subjected to column chromatography on silica gel. The fractions eluted with chloroform-ethyl acetate (1:1, v/v) gave 4-(3,4- dimethoxyphenyl)-6,7-dimethoxy-2-piperidinomethylquinazoline (1.46 g, 65%). This compound was recrystallized from ethyl acetate - hexane. Colorless needles, mp. 130°–132° C.

EXAMPLE 30

According to the same manner as that described in Example 29, 4-(3,4-dimethoxyphenyl)-6,7-dimethoxy-2-morpholinomethylquinazoline was obtained and recrystallized from ethyl acetate - hexane. Colorless prisms, mp. 148°–150° C.

EXAMPLE 31

According to the same manner as that described in Example 29, 2-(N,N-diethylaminomethyl)-4-(3,4-dimethoxyphenyl)-6,7-dimethoxyquinazoline was obtained and recrystallized from ethyl acetate - hexane. Colorless prisms, mp. 111°–113° C.

EXAMPLE 32

According to the same manner as that described in Example 29, ethyl 2-bromomethyl-4-(3,4-dimethoxyphenyl)-6,7-dimethoxyquinoline-3-carboxylate was reacted with N-ethyl-N-propylamine to give ethyl 2-(N-ethyl-N-propylaminomethyl)-4-(3,4-dimethoxyphenyl)-6,7-dimethoxyquinoline-3-carboxylate. Colorless prisms, mp. 105°–106° C.

EXAMPLE 33

A mixture of 2-(2-bromoethyl)-4-(3,4-dimethoxyphenyl)-6,7-dimethoxyquinazoline (0.486 g), diethylamine (0.41 g) and dichloromethane (10 ml) was stirred under reflux for 6 hours. The reaction mixture was poured into water and extracted with dichloromethane. The dichloromethane layer was washed with water and dried over magnesium sulfate, and the solvent was evaporated. The residue was subjected to column chromatography on silica gel. The fractions eluted with chloroform - ethyl acetate (1:1, v/v) gave 2-[2-(N,N-diethylamino)ethyl]-4-(3,4-dimethoxyphenyl)-6,7-dimethoxyquinazoline (0.040 g, 8%). This compound was recrystallized from ethyl acetate - hexane. Colorless prisms, mp. 164°–166° C.

EXAMPLE 34

A mixture of ethyl 2-chloromethyl-4-(3,4-dimethoxyphenyl)-6,7-dimethoxyquinoline-3-carboxylate (3.0 g), N-methyl-N-cyclohexylamine (2.28 g) and ethanol (45 ml) was stirred under reflux for 6 hours. The reaction mixture was poured into water and extracted with dichloromethane. The dichloromethane layer was washed with water and dried over magnesium sulfate, and the solvent was evaporated. The residue was subjected to column chromatography on silica gel. The fractions eluted with chloroform gave ethyl 2-(N-cyclohexyl-N-methylaminomethyl)-4-(3,4-dimethoxyphenyl)-6,7-dimethoxyquinoline-3-carboxylate (2.80 g, 80%). This compound was recrystallized from ethanol. Colorless prisms, mp. 172°–174° C.

EXAMPLES 35 TO 41

According to the same manner as that described in Example 34, the compounds in Table 4 were obtained.

TABLE 4

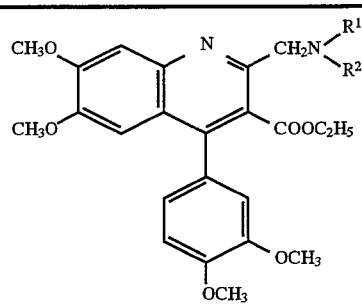

| Ex. No. | $R^1$ | $R^2$ | Yield (%) | mp (°C.) | Recrystallization solvent |
|---|---|---|---|---|---|
| 35 | $C_6H_5CH_2CH_2$ | $C_6H_5CH_2$ | 65 | 135–137 | Ethanol |
| 36 | $C_4H_9$ | $CH_3$ | 64 | 143–144 | Ethanol |
| 37 | $(CH_3)_2CHCH_2$ | $CH_3$ | 44 | 121–123 | Ethyl acetate-Hexane |
| 38 | $C_4H_9$ | $C_2H_5$ | 58 | 113–114 | Ethyl acetate-Hexane |
| 39 | $(C_2H_5)(CH_3)CH$ | $C_3H_7$ | 39 | 129–131 | Ethyl acetate-Hexane |
| 40 | $(CH_3)_3C$ | $C_2H_5$ | 51 | 120–121 | Ethyl acetate-Hexane |
| 41 | $CH_3$ | $C_2H_5$ | 63 | 139–140 | Ethyl acetate-Hexane |

EXAMPLE 42

According to the same manner as that described in Example 14, ethyl 2-chloromethyl-4-(3-isopropoxy-4-methoxyphenyl)-6,7-dimethoxyquinoline-3-carboxylate was reacted with diethylamine to give ethyl 2-(N,N-diethylaminomethyl)-4-(3-isopropoxy-4-methoxyphenyl)-6,7-dimethoxyquinoline-3-carboxylate dihydrochloride. This compound was recrystallized from ethyl acetate - ether. Yellow powder, mp. 122°–124° C.

Elemental Analysis: Calcd. for $C_{29}H_{40}N_2O_6Cl_2 \cdot \frac{1}{2}H_2O$: C,58.78; H,6.97; N,4.73 Found: C,58.84; H,7.00; N,4.69

EXAMPLE 43

According to the same manner as that described in Example 33, ethyl 6-chloro-2-chloromethyl-4-(4-chlorophenyl)quinoline-3-carboxylate was reacted with diethylamine to give ethyl 6-chloro-4-(4-chlorophenyl)-2-(N,N-diethylaminomethyl)quinoline-3-carboxylate. This compound was recrystallized from ethanol. Colorless prisms, mp. 132°–133° C.

EXAMPLE 44

According to the same manner as that described in Example 33, ethyl 6-chloro-2-chloromethyl-4-phenylquinoline-3-carboxylate was reacted with diethylamine to give ethyl 6-chloro-2-(N,N-diethylaminomethyl)-4-phenylquinoline-3-carboxylate. This compound was recrystallized from ethanol. Colorless prisms, mp. 107°–108° C.

EXAMPLE 45

According to the same manner as that described in Example 33, ethyl 2-chloromethyl-4-(3,4-dichlorophenyl)-6,7-dimethoxyquinoline-3-carboxylate was reacted with diethylamine to give ethyl 4-(3,4-dichlorophenyl)-2-(N,N-diethylaminomethyl)-6,7-dimethoxyquinoline-3- carboxylate. This compound was recrystallized from ethyl acetate - hexane. Colorless prisms, mp. 157°–158° C.

EXAMPLE 46

According to the same manner as that described in Example 33, ethyl 2-chloromethyl-4-(4-chlorophenyl)-6,7-dimethoxyquinoline-3-carboxylate was reacted with diethylamine to give ethyl 4-(4-chlorophenyl)-2-(N,N-diethylaminomethyl)-6,7-dimethoxyquinoline-3-carboxylate. This compound was recrystallized from ethyl acetate - hexane. Colorless prisms, mp. 82°–83° C.

EXAMPLE 47

According to the same manner as that described in Example 33, ethyl 2-chloromethyl-4-(4-fluorophenyl)-6,7-dimethoxyquinoline-3-carboxylate was reacted with diethylamine to give ethyl 4-(4-fluorophenyl)-2-(N,N-diethylaminomethyl)-6,7-dimethoxyquinoline-3-carboxylate. This compound was recrystallized from ethyl acetate - hexane. Colorless prisms, mp. 102°–103° C.

EXAMPLE 48

According to the same manner as that described in Example 33, ethyl 2-chloromethyl-4-(4-methoxyphenyl)-6,7-dimethoxyquinoline-3-carboxylate was reacted with diethylamine to give ethyl 2-(N,N-diethylaminomethyl)-6,7-dimethoxy-4-(4-methoxyphenyl)quinoline-3-carboxylate. This compound was recrystallized from ethyl acetate - hexane. Colorless prisms, mp. 118°–119° C.

EXAMPLE 49

A mixture of 2-amino-4,5,3',4'-tetramethoxybenzophenone hydrochloride (7.7 g), ethyl 6-(N,N-diethylamino)-3-oxohexanoate (5.0 g) and ethanol (100 ml) was stirred under reflux for 4 hours. The reaction mixture was concentrated under reduced pressure, and the residue was dissolved in chloroform. The chloroform layer was washed with an aqueous saturated solution of sodium bicarbonate and water and dried over magnesium sulfate, and the solvent was evaporated. The residue was subjected to column chromatography on silica gel. The fractions eluted with chloroform-methanol (20:1, v/v) gave ethyl 2-[3-(N,N-diethylamino)propyl]-4-(3,4-dimethoxyphenyl)-6,7-dimethoxyquinoline-3-carboxylate (1.51 g, 14%). This compound was recrystallized from ethanol-hexane. Colorless prisms, mp. 96°–98° C.

EXAMPLE 50

According to the same manner as that described in Example 49, 2-amino-4,5,3',4'-tetramethoxybenzophenone hydrochloride was reacted with ethyl 7-(N,N-diethylamino)-3-oxoheptanoate to give ethyl 2-[4-(N,N-diethylamino)butyl]-4-(3,4-dimethoxyphenyl)-6,7-dimethoxyquinoline-3-carboxylate. This compound was recrystallized from ethyl acetate - hexane. Colorless prisms, mp. 171°–172° C.

EXAMPLE 51

A mixture of ethyl 2-(2-bromoethyl)-4-(3,4-dimethoxyphenyl)-6,7-dimethoxyquinoline-3-carboxylate (0.45 g), diethylamine (0.326 g) and dichloromethane (10 ml) was stirred under reflux for 14 hours. The reaction mixture was washed with water and dried over magnesium sulfate, and the solvent was evaporated under reduced pressure. The residue was subjected to column chromatography on silica gel. The fractions eluted with chloroform-methanol (20:1, v/v) gave ethyl 2-[2-(N,N-diethylamino)ethyl]-4-(3,4-dimethoxyphenyl)-6,7-dimethoxyquinoline-3-carboxylate (0.113 g, 26%). This compound was recrystallized from ethyl acetate - hexane. Colorless prisms, mp. 76°–78° C.

EXAMPLE 52

According to the same manner as that described in Example 33, ethyl 2-chloromethyl-4-(3,4-dimethoxyphenyl)-6,7-dimethoxyquinoline-3-carboxylate 1-oxide was reacted with diethylamine to give ethyl 2-(N,N-diethylaminomethyl)-4-(3,4-dimethoxyphenyl)-6,7-dimethoxyquinoline-3-carboxylate 1-oxide. This compound was recrystallized from ethanol. Colorless prisms, mp. 143°–144° C.

EXAMPLE 53

According to the same manner as that described in Example 33, ethyl 2-chloromethyl-4-(3,4-dimethoxyphenyl)-6,7-dimethoxyquinoline-3-carboxylate was reacted with diisopentylamine to give ethyl 4-(3,4-dimethoxyphenyl)-2-(N,N-diisopentylaminomethyl)-6,7-dimethoxyquinoline-3-carboxylate. This compound was recrystallized from ethyl acetate - hexane. Colorless prisms, mp. 114°–115° C.

EXAMPLE 54

A mixture of 2-chloromethyl-4-(3,4-dimethoxyphenyl)-6,7-dimethoxyquinazoline (10.0 g), ethylamine (70% aqueous solution, 206 g) and ethanol (200 ml)—dichloromethane (200 ml) was stirred at room temperature for 13 hours. The reaction mixture was concentrated under reduced pressure, and the residue was dissolved in dichloromethane. The dichloromethane layer was washed with water and dried over magnesium sulfate, and the solvent was evaporated under reduced pressure. The residue was subjected to column chromatography on silica gel. The fractions eluted with chloroform - ethanol (5:1, v/v) gave 2-(N-ethylaminomethyl-4-(3,4-dimethoxyphenyl)-6,7-dimethoxyquinazoline (5.7 g, 55%). This compound was recrystallized from ethanol. Colorless prisms, mp. 128°–130° C.

EXAMPLE 55

According to the same manner as that described in Example 34, ethyl 2-chloromethyl-4-(3,4-dimethoxyphenyl)-6,7-dimethoxyquinoline-3-carboxylate was reacted with N-methylaniline to give ethyl 4-(3,4-dimethoxyphenyl)-2-(N-methyl-N-phenylaminomethyl)-6,7-dimethoxyquinoline-3-carboxylate. This compound was recrystallized from dichloromethane-hexane. Colorless prisms, mp. 194°–196° C.

EXAMPLE 56

A mixture of 2-chloromethyl-4-(3,4-dimethoxyphenyl)-6,7-dimethoxyquinazoline (1.78 g), tert-butylamine (17.4 g) and dichloromethane (40 ml) was stirred at room temperature for 13 hours. The reaction mixture was washed with water, dried over magnesium sulfate, and concentrated under reduced pressure. The residue was subjected to column chromatography on silica gel. The fractions eluted with dichloromethane-ethanol (30:1, v/v) gave 2-(tert-butylaminomethyl)-4-(3,4-dimethoxyphenyl)-6,7-dimethoxyquinazoline (0.77 g, 40%). This compound was recrystallized from ethyl acetate - hexane. Colorless prisms, mp. 120°–122° C.

EXAMPLE 57

According to the same manner as that described in Example 56, 2-chloromethyl-4-(3,4-dimethoxyphenyl)-6,7-dimethoxyquinazoline was reacted with sec-butylamine to give 2-(sec-butylaminomethyl)-4-(3,4-dimethoxyphenyl)-6,7-dimethoxyquinazoline. This compound was recrystallized from ethyl acetate - hexane. Colorless prisms, mp. 118°–120° C.

EXAMPLE 58

According to the same manner as that described in Example 56, 2-chloromethyl-4-(3,4-dimethoxyphenyl)-6,7-dimethoxyquinazoline was reacted with N-methylaniline to give 4-(3,4-dimethoxyphenyl)-6,7-dimethoxy-2-(N-methyl-N-phenylaminomethyl)quinazoline. This compound was recrystallized from ethanol. Colorless needles, mp. 141°–143° C.

EXAMPLE 59

According to the same manner as that described in Example 56, 2-chloromethyl-4-(3,4-dimethoxyphenyl)-6,7-dimethoxyquinazoline was reacted with aniline to give 2-anilinomethyl-4-(3,4-dimethoxyphenyl)-6,7-dimethoxyquinazoline. This compound was recrystallized from ethanol. Colorless prisms, mp. 199°–200° C.

EXAMPLE 60

A mixture of ethyl 2-chloromethyl-4-(3,4-dimethoxyphenyl)-6,7-dimethoxyquinoline-3-carboxylate (1.0 g), 2-(methylamino)pyridine (0.95 g) and 2-methoxyethanol (30 ml) was stirred under reflux for 17 hours. The reaction mixture was concentrated under reduced pressure. Water was added to the residue, and the resulting mixture was extracted with ethyl acetate. The ethyl acetate layer was washed with water, dried over magnesium sulfate, and concentrated under reduced pressure. The residue was subjected to column chromatography on silica gel. The fractions eluted with hexane - ethyl acetate (3:2, v/v) gave ethyl 4-(3,4-dimethoxyphenyl)-6,7-dimethoxy-2-[N-methyl-N-(2-pyridyl)aminomethyl]quinoline-3-carboxylate (0.1 g, 9%). This compound was recrystallized from dichloromethane-ethanol. Pale yellow prisms, mp. 174°–175° C.

EXAMPLE 61

Sodium hydride (oily, 60%, 0.129 g) was added to a solution of diphenylamine (0.497 g) in N,N-dimethylformamide (10 ml), and the mixture was stirred at room temperature for 20 minutes. Then, 2-chloromethyl-4-(3,4-dimethoxyphenyl)-6,7-dimethoxyquinazoline (1.0 g) was added, and the mixture was stirred at 100° C. for 4 hours. The reaction mixture was poured into water, and extracted with ethyl acetate. The ethyl acetate layer was washed with water, dried over magnesium sulfate, and concentrated under reduced pressure. The residue was subjected to column chromatography on silica gel. The fractions eluted with ethyl acetate - hexane (1:1, v/v) gave 2-(N,N-diphenylaminomethyl)-4-(3,4-dimethoxyphenyl)-6,7-dimethoxyquinazoline (0.27 g, 20%). This compound was recrystallized from ethyl acetate - hexane. Colorless prisms, mp. 215°–216° C.

What is claimed is:

1. A pharmaceutical composition comprising a compound of the formula (I):

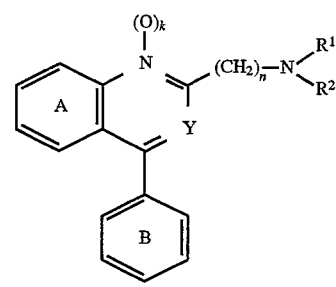

wherein

Y is a nitrogen atom or C—G in which G is an optionally esterified carboxyl group;

$R^1$ and $R^2$ are each independently a hydrogen atom, optionally substituted hydrocarbon group or optionally substituted heterocyclic group, or $R^1$ and $R^2$ are linked together to form a saturated ring;

wherein the ring A is substituted with lower alkylenedioxy at the 6- and 7-positions of the quinoline or quinazoline ring, or the ring A is substituted with at least one alkoxy group;

the ring B may optionally be substituted;

n is an integer of 1 to 4; and k is 0 or 1, or a pharmaceutically acceptable salt thereof; and a pharmaceutically acceptable carrier.

2. The pharmaceutical composition according to claim 1, wherein the optionally substituted hydrocarbon group represented by $R^1$ and $R^2$ is an optionally substituted alkyl group.

3. The pharmaceutical composition according to claim 1, wherein $R^1$ and $R^2$ are linked together to form a 5- to 7-membered saturated ring.

4. The pharmaceutical composition according to claim 1, wherein n is 1 or 2.

5. The pharmaceutical composition according to claim 1, wherein Y is C—G.

6. The pharmaceutical composition according to claim 5, wherein G is $C_{1-6}$ alkyloxycarbonyl.

7. The pharmaceutical composition according to claim 6, wherein G is ethoxycarbonyl.

8. The pharmaceutical composition according to claim 1, wherein Y is a nitrogen atom.

9. The pharmaceutical composition according to claim 1 which is an anti-inflammatory pharmaceutical composition.

10. The pharmaceutical composition according to claim 1, wherein the ring A is substituted with methylenedioxy at the 6- and 7-positions of the quinoline or quinazoline ring.

11. A method of treating an inflammatory disease in a mammal which comprises administering to such mammal in need thereof an effective amount of a compound of the formula (I):

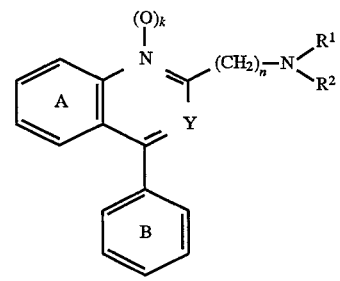

wherein

Y is a nitrogen atom or C—G in which G is an optionally esterified carboxyl group;

$R^1$ and $R^2$ are each independently a hydrogen atom, optionally substituted hydrocarbon group or optionally substituted heterocyclic group, or $R^1$ and $R^2$ are linked together to form a saturated ring;

each of the ring A and ring B may optionally be substituted;

n is an integer of 1 to 4; and k is 0 or 1;

or a pharmaceutically acceptable salt thereof.

12. The pharmaceutical composition according to claim 1, wherein the ring A is substituted with at least one methoxy group.

13. The pharmaceutical composition according to claim 1, wherein the ring A is substituted with the same or different two alkoxy groups.

14. The pharmaceutical composition according to claim 13, wherein the ring A is substituted with two methoxy groups.

15. The pharmaceutical composition according to claim 14, wherein the ring A is substituted with two methoxy groups at the 6- and 7-positions of the quinoline or quinazoline ring.

16. The pharmaceutical composition according to claim 1, wherein the ring B is substituted with lower alkylenedioxy.

17. The pharmaceutical composition according to claim 16, wherein the ring B is substituted with methylenedioxy.

18. The pharmaceutical composition according to claim 1, wherein the ring B is substituted with at least one alkoxy group.

19. The pharmaceutical composition according to claim 1, wherein the ring B is substituted with at least one methoxy group.

20. The pharmaceutical composition according to claim 1, wherein the ring B is substituted with the same or different two alkoxy groups.

21. The pharmaceutical composition according to claim 20, wherein the ring B is substituted with two methoxy groups.

22. The pharmaceutical composition according to claim 21, wherein the ring B is substituted with two methoxy groups at the 3- and 4- positions.

23. The pharmaceutical composition according to claim 1, wherein k is 0.

24. The pharmaceutical composition according to claim 1, wherein the compound of the formula (I) is ethyl 4-(3,4-dimethoxyphenyl)-2-(N-sec-butyl-N-propylaminomethyl)-6,7-dimethoxyquinoline-3-carboxylate;

ethyl 4-(3,4-dimethoxyphenyl)-2-(N-tert-butyl-N-ethylaminomethyl)-6,7-dimethoxyquinoline-3-carboxylate;

ethyl 2-(N,N-diethylaminomethyl)-4-(3,4-dimethoxyphenyl)-6,7-dimethoxyquinoline-3-carboxylate; or 4-(3,4-dimethoxyphenyl)-2-(N-ethylaminomethyl)-6,7-dimethoxyquinazoline.

25. A compound of the formula (I'):

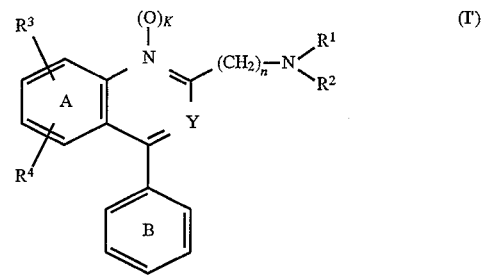

wherein
Y is a nitrogen atom or C—G in which G is an optionally esterified carboxyl group;

$R^1$ and $R^2$ are each independently a hydrogen atom, optionally substituted hydrocarbon group or optionally substituted heterocyclic group, or $R^1$ and $R^2$ are linked together to form a saturated ring;

$R^3$ and $R^4$ are each independently an alkoxy group or $R^3$ and $R^4$ are linked together to form a $C_{1-3}$ alkylenedioxy group at the 6- and 7-positions of the quinoline or quinazoline ring;

the ring B may optionally be substituted;

n is an integer of 1 to 4; and k is 0 or 1;

or a salt thereof.

26. The compound according to claim 25, wherein $R^3$ and $R^4$ are each methoxy.

27. The compound according to claim 25, wherein $R^3$ and $R^4$ are each methoxy at the 6- and 7-positions of the quinoline or quinazoline ring.

28. The compound according to claim 25, wherein the ring B is substituted with at least one alkoxy group.

29. The compound according to claim 25, wherein the ring B is substituted with at least one methoxy group.

30. The compound according to claim 25, wherein the ring B is substituted with the same or different two alkoxy groups.

31. The compound according to claim 25, wherein the ring B is substituted with two methoxy groups.

32. The compound according to claim 25, wherein the ring B is substituted with two methoxy groups at the 3- and 4-positions.

33. The compound according to claim 25, which is ethyl 4-(3,4-dimethoxyphenyl)-2-(N-sec-butyl-N-propylaminomethyl)-6,7-dimethoxyquinoline-3-carboxylate;

ethyl 4-(3,4-dimethoxyphenyl)-2-(N-tert-butyl-N-ethylaminomethyl)-6,7-dimethoxyquinoline-3-carboxylate;

ethyl 2-(N,N-diethylaminomethyl)-4-(3,4-dimethoxyphenyl)-6,7-dimethoxyquinoline-3-carboxylate; or 4-(3,4-dimethoxyphenyl)-2-(N-ethylaminomethyl)-6,7-dimethoxyquinazoline.

34. A method according to claim 11, wherein the inflammatory disease is arthritis.

35. The method according to claim 11, wherein the ring B is substituted with two alkoxy groups which may be the same or different.

36. The method according to claim 35, wherein the ring B is substituted with two methoxy groups.

37. The method according to claim 36, wherein the ring B is substituted with two methoxy groups as the 3- and 4-positions.

38. The method according to claim 11, wherein k is 0.

39. The method according to claim 11, wherein the compound of the formula (I) is ethyl 4-(3,4-dimethoxyphenyl)-2-(N-sec-butyl-N-propylaminomethyl)-6,7-dimethoxyquinoline-3-carboxylate;

ethyl 4-(3,4-dimethoxyphenyl)-2-(N-tert-butyl-N-ethylaminomethyl)-6,7-dimethoxyquinoline-3-carboxylate;

ethyl 2-(N,N-diethylaminomethyl)-4-(3,4-dimethoxyphenyl)-6,7-dimethoxyquinoline-3-carboxylate; or 4-(3,4-dimethoxyphenyl)-2-(N-ethylaminomethyl)-6,7-dimethoxyquinazoline.

40. The method according to claim 11, wherein the optionally substituted hydrocarbon group represented by $R^1$ and $R^2$ is an optionally substituted alkyl group.

41. The method according to claim 11, wherein $R^1$ and $R^2$ are linked together to form a 5- to 7-membered saturated ring.

42. The method according to claim 11, wherein n is 1 or 2.

43. The method according to claim 11, wherein Y is C—G.

44. The method according to claim 43, wherein G is $C_{1-6}$ alkyloxycarbonyl.

45. The method according to claim 44, wherein G is ethoxycarbonyl.

46. The method according to claim 11, wherein Y is a nitrogen atom.

47. The method according to claim 11, wherein the ring A is substituted with lower alkylenedioxy at the 6- and 7-positions of the quinoline or quinazoline ring.

48. The method according to claim 11, wherein the ring A is substituted with methylene dioxy at the 6- and 7-positions of the quinoline or quinazoline ring.

49. The method according to claim 11, wherein the ring A is substituted with at least one alkoxy group.

50. The method according to claim 11, wherein the ring A is substituted with at least one methoxy group.

51. The method according to claim 11, wherein the ring A is substituted with two alkoxy groups which may be the same or different.

52. The method according to claim 51, wherein the ring A is substituted with two methoxy groups.

53. The method according to claim 52, wherein the ring A is substituted with two methoxy groups at the 6- and 7-positions of the quinoline or quinazoline ring.

54. The method according to claim 11, wherein the ring B is substituted with lower alkylenedioxy.

55. The method according to claim 54, wherein the ring B is substituted with methylenedioxy.

56. The method according to claim 11, wherein the ring B is substituted with at least one alkoxy group.

57. The method according to claim 11, wherein the ring B is substituted with at least one methoxy group.

* * * * *